(12) United States Patent
Zeng

(10) Patent No.: US 11,980,629 B2
(45) Date of Patent: *May 14, 2024

(54) CONDITIONING REGIMENS AND METHODS FOR INDUCING MIXED CHIMERISM

(71) Applicant: CITY OF HOPE, Duarte, CA (US)

(72) Inventor: Defu Zeng, Arcadia, CA (US)

(73) Assignee: CITY OF HOPE, Duarte, CA (US)

( * ) Notice: Subject to any disclaimer, the term of this patent is extended or adjusted under 35 U.S.C. 154(b) by 82 days.

This patent is subject to a terminal disclaimer.

(21) Appl. No.: 17/399,871

(22) Filed: Aug. 11, 2021

(65) Prior Publication Data

US 2022/0031716 A1 Feb. 3, 2022

Related U.S. Application Data

(63) Continuation of application No. 15/775,358, filed as application No. PCT/US2016/061382 on Nov. 10, 2016, now Pat. No. 11,116,777.

(60) Provisional application No. 62/253,657, filed on Nov. 10, 2015.

(51) Int. Cl.
| | |
|---|---|
| *A61K 31/675* | (2006.01) |
| *A61K 31/7056* | (2006.01) |
| *A61K 35/14* | (2015.01) |
| *A61K 35/17* | (2015.01) |
| *A61K 35/26* | (2015.01) |
| *A61K 35/28* | (2015.01) |
| *A61K 39/395* | (2006.01) |
| *A61P 37/06* | (2006.01) |
| *C07K 16/28* | (2006.01) |

(52) U.S. Cl.
CPC ........ *A61K 31/675* (2013.01); *A61K 31/7056* (2013.01); *A61K 35/14* (2013.01); *A61K 35/17* (2013.01); *A61K 35/26* (2013.01); *A61K 35/28* (2013.01); *A61K 39/39516* (2013.01); *A61P 37/06* (2018.01); *C07K 16/2809* (2013.01); *A01K 2207/20* (2013.01); *A01K 2227/105* (2013.01); *A01K 2267/0387* (2013.01)

(58) Field of Classification Search
None
See application file for complete search history.

(56) References Cited

U.S. PATENT DOCUMENTS

| | | | | |
|---|---|---|---|---|
| 7,037,900 | B2 * | 5/2006 | DiMartino | ......... A61K 31/7056 514/45 |
| 11,116,777 | B2 * | 9/2021 | Zeng | ...................... A61K 35/26 |
| 2001/0048921 | A1 | 12/2001 | Sykes et al. | |
| 2003/0031652 | A1 | 2/2003 | Hering et al. | |
| 2003/0099622 | A1 | 5/2003 | Hering et al. | |
| 2004/0023885 | A1 | 2/2004 | Brand et al. | |
| 2006/0127399 | A1 | 6/2006 | Zeng | |
| 2012/0148577 | A1 | 6/2012 | Fuchs et al. | |
| 2015/0218522 | A1 | 8/2015 | Peterson et al. | |

OTHER PUBLICATIONS

Kim et al. 'Treatment Options in Steroid-Refractory Acute Graft-Versus-Host Disease Following Hematopoietic Stem Cell Transplantation.' Ann Pharmacother 2007:41:1436-44. Published Online, Aug. 7, 2007, www.theannals.com, DOI! 10.1345/aph.1K179.*
European Patent Office, Extended European Search Report and Opinion dated Dec. 3, 2021 for European Patent Application No. 21178717.1, 9 pages.
Ikehara, S., "Bone Marroe Transplantation for Autoimmune Diseases," Acta Haematol. 99:116-132 (1998).
Seung, E., et al., "Allogenic Hematopoietic Chimerism in Mice Treated with Sublethal Myeloablation and Anti-CD154 Antibody: Absence of Graft-Versus-Host Disease, Induction of Skin Allograft Tolerance, and Prevention of Recurrent Autoimmunity in Islet-Allografted NOD/Lt Mice," Blood 95:2175-2182 (2000).
Walters, M. C., et al., "Bone Marrow Transplantation for Sickle Cell Disease," New Engl. J. Med. 335(6):369-376 (1996).
Atkins, H. L., et al., "Hematopoietic Stem Cell Therapy for Multiple Sclerosis: Top 10 Lessons Learned," Neurotherapeutics 10:68-76 (2013).
Baeyens, L., et al., "In Vitro Generation of Insulin-Producing Beta Cells from Adult Exocrine Pancreatic Cells," Diabetologia 48:49-57 (2005).
Beilhack, G. F., et al., "Prevention of Type 1 Diabetes with Major Histocompatibility Complex-Compatible and Nonmarrow Ablative Hematopoietic Stem Cell Transplants," Diabetes 54:1770-1779 (2005).
Bettelli, E., et al., "TH-17 Cells in the Circle of Immunity and Autoimmunity," Nat. Immunol. 8(4):345-350 (2007).
Bluestone, J. A., et al., "Natural Versus Adaptive Regulatory T Cells," Nat. Rev. Immunol. 3:253-257 (2003).

(Continued)

*Primary Examiner* — Nora M Rooney
(74) *Attorney, Agent, or Firm* — Perkins Coie LLP; Lara J. Dueppen; Allison M. Glasunow

(57) ABSTRACT

Disclosed herein are conditioning regimens and methods for inducing MHC- or HLA-mismatched mixed chimerism by conditioning a recipient with radiation-free, low-doses of cyclophosphamide (CY), pentostatin (PT), and anti-thymocyte globulin (ATG) prior to transplantation of donor bone marrow cells. In certain embodiments, the donor bone marrow cells may be CD4+ T-depleted bone marrow cells. The conditioning regimens and methods may also include administering one or more populations of conditioning donor cells selected from donor $CD4^+$ T-depleted spleen cells, donor $CD8^+$ T cells, and donor G-CSF-mobilized peripheral blood mononuclear cells. The conditioning regimen is clinically acceptable and can be used for treating hereditary hematological diseases and autoimmune diseases, as well as for promoting organ transplantation immune tolerance.

10 Claims, 18 Drawing Sheets

(56) References Cited

OTHER PUBLICATIONS

Bonner-Weir, S., et al., "In Vitro Cultivation of Human Islets from Expanded Ductal Tissue," Proc. Natl. Acad. Sci. 97(14):7999-8004 (2000).

Bowen, J. D., et al., "Autologous Hematopoietic Cell Transplantation Following High-Dose Immunosuppressive Therapy for Advanced Multiple Sclerosis: Long-Term Results," Bone Marrow Transplant. 47(7):946-951 (2012).

Castano, L., et al., "Type-1 Diabetes: A Chronic Autoimmune Disease of Human, Mouse, and Rat," Annu. Rev. Immunol. 8:647-679 (1990).

Chen, S.H., et al., "Adenosine Deaminase Deficiency: Disappearance of Adenine Deoxynucleotides from a Patient's Erythrocytes After Successful Marrow Transplantation," J. Clin. Invest. 62:1386-1389 (1978).

Chung, C.H., et al., "Pancreatic B-Cell Neogenesis by Direct Conversion from Mature a-Cells," Stem Cells 28:1630-1638 (2010).

Collombat, P., et al., "The Ectopic Expression of Pax4 in the Mouse Pancreas Converts Progenitor Cells into α- and subsequently β-Cells," Cell 138(3):449-462 (2009).

Criscimanna, A., et al., "Duct Cells Contribute to Regeneration of Endocrine and Acinar Cells Following Pancreatic Damage in Adult Mice," Gastroenterol. 141(4):1451-1462 (2011).

Daikeler, T., et al., "Secondary Autoimmune Diseases Occurring After HSCT for an Autoimmune Disease: A Retrospective Study of the EBMT Autoimmune Disease Working Party," Blood doi: 10.1182/blood-2011-02-336156 (2011).

Deng, R., et al., "B7H1/CD80 Interaction Augments PD-1-Dependent T Cell Apoptosis and Ameliorates Graft Versus Host Disease," J. Immunol. 194(2):560-574 (2015).

Dezern, A. E., et al., "Repeated Treatment with High Dose Cyclophosphamide for Severe Autoimmune Diseases," Am. J. Blood Res. 3(1):84-90 (2013).

Dezern, A. E., et al., "High Dose Cyclophosphamide without Stem Cell Rescue in 207 Patients with Aplastic anemia and other Autoimmune Diseases," Medicine 90(2):89-98 (2011).

Ding, L., et al., "β-Cell Differentiation and Regeneration in Type 1 Diabetes," Diabetes, Obesity and Metabolism 15(Suppl. 3):98-104 (2013).

Dor, Y., et al., "Adult Pancreatic β-Cells are Formed by Self-Duplication Rather than Stem-Cell Differentiation," Nature 429:41-46 (2004).

European Patent Office, Extended European Search Report and Opinion dated Jun. 11, 2019 for European Patent Application No. 16865024.0.

Farge, D., et al., "Autologous Hematopoietic Stem Cell Transplantation for Autoimmune Diseases: An Observational Study on 12 years' Experience from the European Group for Blood and Marrow Transplantation Working Party on Autoimmune Diseases," Haematologica 95:284-292 (2010).

Fassas, A., et al., "Long-Term Results of Stem Cell Transplantation for MS," Neurology 76:1066-1070 (2011).

Fernandes, A., et al., "Differentiation of New Insulin-Producing Cells is Induced by Injury in Adult Pancreatic Islets," Endocrinol. 138(4):1750-1762 (1997).

Fiorina, P., et al., "The Clinical Impact of Islet Transplantation," Am. J. Transplant. 8:1990-1997 (2008).

Font-Burgada, J., et al., "Hybrid Periportal Hepatocytes Regenerate the Injured Liver without Giving Rise to Cancer," Cell 162(4):766-779 (2015).

Frisullo, G., et al., "Regulatory T Cells Fail to Suppress CD4+ T-Bet+ T Cells in Relapsing Multiple Sclerosis Patients," Immunology 127:418-428 (2008).

Furuyama, K., et al., "Continuous Cell Supply from a Sox9-Expressing Progenitor Zone in Adult Liver, Exocrine Pancreas and Intestine," Nat. Genet. 43(1):34-43 (2011).

Gagnerault, M. C., et al., "Autoimmunity During Thymectomy-Induced Lymphopenia: Role of Thymus Ablation and Initial Effector T Cell Activation Timing in Nonobese Diabetic Mice," J. Immunol. 183:4913-4920 (2009).

Griffin, K. J., et al., "Combination Therapy with Sitagliptin and Lansoprazole in Patients with Recent-Onset Type 1 Diabetes (REPAIR-T1D): 12-Month Results of a Multicentre, Randomised, Placebo-Controlled, Phase 2 Trial," Lancet Diabetes Endocrinol. 2:710-718 (2014).

Griffith, L. M., et al., "Feasibility of Allogeneic Hematopoietic Stem Cell Transplantation for Autoimmune Disease: Position Statement from a National Institute of Allergy and Infectious Diseases and National Cancer Institute-Sponsored International Workshop, Bethesda, MD, Mar. 12 and 13, 2005," Biol. Blood Marrow Transplant. 11:862-870 (2005).

Guz, Y., et al., "Regeneration of Pancreatic β Cells from Intra-Islet Precursor Cells in an Experimental Model of Diabetes," Endocrinol. 142(11):4956-4968 (2001).

Haas, J., et al., "Reduced Suppressive Effect of $CD4+CD25^{high}$ Regulatory T Cells on the T Cell Immune Response Against Myelin Oligodendrocyte Glycoprotein in Patients with Multiple Sclerosis," Eur. J. Immunol. 35:3343-3352 (2005).

Hafler, D. A., et al., "Multiple Sclerosis," Immunol. Rev. 204:208-231 (2005).

Hart, A. W., et al., "The Developmental Regulator Pax6 Is Essential for Maintenance of Islet Cell Function in the Adult Mouse Pancreas," PLoS One 8(1):e54173 (2013).

Hassan, R., et al., "Major Cancer Regressions in Mesothelioma After Treatment with an Anti-Mesothelin Immunotoxin and Immune Suppression," Science Translational Medicine 5(208):208ra147 (2013).

Houbracken, I., et al., "Lineage Tracing of Pancreatic Stem Cells and Beta Cell Regeneration," Methods Mol. Biol. 933:303-315 (2012).

Huan, J., et al., "Decreased FOXP3 Levels in Multiple Sclerosis Patients," J. Neurosci. Res. 81:45-52 (2005).

Iidstad, S. T., et al., "Preconditioning of NOD Mice with Anti-CD8 mAb and Costimulatory Blockade Enhances Chimerism and Tolerance and Prevents Diabetes, While Depletion of αβ-TCR+ and CD4+ Cells Negates the Effect," Blood 105:2577-2584 (2005).

Inada, A., et al., "Carbonic Anhydrase II-Positive Pancreatic Cells are Progenitors for Both Endocrine and Exocrine Pancreas After Birth," Proc. Natl. Acad. Sci. 105(50):19915-19919 (2008).

Jin, L., et al., "Colony-Forming Cells in the Adult mouse pancreas are Expandable in Matrigel and Form Endocrine/Acinar Colonies in Laminin Hydrogel," Proc. Natl. Acad. Sci. 110(10):3907-3912 (2013).

Jin, L., et al., "In Vitro Multilineage Differentiation and Self-Renewal of Single Pancreatic Colony-Forming Cells from Adult C57Bl/6 Mice," Stem Cells Devel. 23(8):899-909 (2014).

Jordan, M. S., et al., "Thymic Selection of CD4+CD25+ Regulatory T Cells Induced by an Agonist Self-Peptide," Nat. Immunol. 2(4):301-306 (2001).

Koblas, T., et al., "An Acidic pH and Activation of Phosphoinositide 3-Kinase Stimulate Differentiation of Pancreatic Progenitors Into Insulin-Producing Cells," Transplantation Proceedings 42:2075-2080 (2010).

Kopinke, D., et al., "Exocrine-to-Endocrine Differentiation is Detectable Only Prior to Birth in the Uninjured Mouse Pancreas," BMC Devel. Biol. 10:38 (2010).

Kopp, J. L., et al., "Progenitor Cell Domains in the Developing and Adult Pancreas," Cell Cycle 10(12):1921-1927 (2011).

Kopp, J. L., et al., "Sox9+ Ductal Cells are Multipotent Progenitors Throughout Development But Do Not Produce New Endocrine Cells in the Normal or Injured Adult Pancreas," Development 138:653-665 (2011).

Krasulova, E., et al., "High-Dose Immunoablation with Autologous Haematopoietic Stem Cell Transplantation in Aggressive Multiple Sclerosis: A Single Centre 10-Year Experience," Multiple Sclerosis 16(6):685-693 (2010).

Krishnamoorthy, G., et al., "Spontaneous Opticospinal Encephalomyelitis in a Double-Transgenic Mouse Model of Autoimmune T Cell/B Cell Cooperation," J. Clin. Invest. 116(9):2385-2392 (2006).

Kronenberg, M., et al., "Regulation of Immunity by Self-Reactive T Cells," Nature 435:598-604 (2005).

Kuchroo, V. K., et al., "T Cell Response in Experimental Autoimmune Encephalomyelitis (EAE): Role of Self and Cross-Reactive

(56) References Cited

OTHER PUBLICATIONS

Antigens in Shaping, Tuning, and Regulating the Autopathogenic T Cell Repertoire," Annu. Rev. Immunol. 20:101-123 (2002).
Lan, F., et al., "Host Conditioning with Total Lymphoid Irradiation and Antithymocyte Globulin Prevents Graft-versus-Host Disease: The Role of CD1-Reactive Natural Killer T Cells," Biol. Blood Marrow Transplant. 9:355-363 (2003).
Lange, C., et al., "CD62L$^{high}$ Treg Cells with Superior Immunosuppressive Properties Accumulate within the CNS During Remissions of EAE," Brain, Behavior, and Immunity 25:120-126 (2011).
Li, H., et al., "Mixed Allogenic Chimerism Induced by a Sublethal Approach Prevents Autoimmune Diabetes and Reverses Insulitis in Nonobese Diabetic (NOD) Mice," J. Immunol. 156:380-388 (1996).
Li, N., et al., "HDAC Inhibitor Reduces Cytokine Storm and Facilitates Induction of Chimerism that Reverses Lupus in Anti-CD3 Conditioning Regimen," Proc. Natl. Acad. Sci. 105(12): 4796-4801 (2008).
Li, W., et al., "Long-Term Persistence and Development of Induced Pancreatic Beta Cells Generated by Lineage Conversion of Acinar Cells," Nat. Biotechnol. 32(12): 1223-1230 (2014).
Liang, Y., et al., "Donor CD8+ T Cells Facilitate Induction of Chimerism and Tolerance Without GVHD in Autoimmune NOD Mice Conditioned with Anti-CD3 mAb," Blood 105:2180-2188 (2005).
Liston, A., et al., "Differentiation of Regulatory Foxp3+ T Cells in the Thymic Cortex," Proc. Natl. Acad. Sci. 105(33):11903-11908 (2008).
Lu, J.Q., et al., "Continued Disease Activity in a Patient with Multiple Sclerosis After Allogenic Hematopoietic Cell Transplantation," Arch. Neurol. 66(1):116-120 (2009).
Luznik, L., et al., "Post-Transplantation Cyclophosphamide for Tolerance Induction in HLA-Haploidentical BMT," Semin. Oncol. 39(6):1-16 (2012).
Lysy, P. A., et al., "Concise Review: Pancreas Regeneration: Recent Advances and Perspectives," Stem Cells Translational Medicine 1:150-159 (2012).
Mancardi, G.L., et al., "Autologous Haematopoietic Stem Cell Transplantation with an Intermediate Intensity Conditioning Regimen in Multiple Sclerosis: the Italian Multi-Centre Experience," Mult. Scler. J. 18(6):835-842 (2012).
Mariotti, J., et al., "The Pentostatin Plus Cyclophosphamide (PC) Nonmyeloablative Regimen Induces Durable Host T Cell Functional Deficits and Prevents Murine Marrow Allograft Rejection," Biol. Blood Marrow Transplant. 17(5):620-631 (2011).
Minami, K., et al., "Lineage Tracing and Characterization of Insulin-Secreting Cells Generated from Adult Pancreatic Acinar Cells," Proc. Natl. Acad. Sci. 102(42):15116-15121 (2005).
Mitchell, A. J., et al., "Quality of Life and Its Assessment in Multiple Sclerosis: Integrating Physical and Psychological Components of Wellbeing," Lancet Neurol. 4:556-566 (2005).
Nikolic, B., et al., "Mixed Hematopoietic Chimerism Allows Cure of Autoimmune Diabetes Through Allogeneic Tolerance and Reversal of Autoimmunity," Diabetes 53:376-383 (2004).
Ommati, L.V.M., et al., "Characteristics of Two Conditioning Regimens Cyclophosphamide Plus Antithymocyte Globulin Versus Cyclophosphamide Plus Busulfan in Allogenic Stem Cell Transplantation for Severe Aplastic Anemia," Biol. Blood Marrow Transplant. 13(2):95-96 (2006).
Pan, F. C., et al., "Spatiotemporal Patterns of Multipotentiality in Ptf1a-Expressing Cells During Pancreas Organogenesis and Injury-Induced Facultative Restoration," Development 140:751-764 (2013).
Pang, K., et al., "Beta Cells Arise from Glucose Transporter Type 2 (Glut2)-Expressing Epithelial Cells of the Developing Rat Pancreas," Proc. Natl. Acad. Sci. USA 91:9559-9563 (1994).
Pasquini, M. C., et al., "Hematopoietic Stem Cell Transplantation for Multiple Sclerosis: Collaboration of the CIBMTR and EBMT to Facilitate International Clinical Studies," Biol. Blood Marrow Transplant. 16(8):1076-1083 (2010).
Peters, A., et al., "Th17 Cells Induce Ectopic Lymphoid Follicles in Central Nervous System Tissue Inflammation," Immunity 35(6):986-996 (2011).
Racine, J., et al., "Induction of Mixed Chimerism With MHC-Mismatched but Not Matched Bone Marrow Transplants Results in Thymic Deletion of Host-Type Autoreactive T-Cells in NOD Mice," Diabetes 60:555-564 (2011).
Racine, J., et al., "Induction of Mixed Chimerism Depletes Pre-Existing and De Novo Developed Autoreactive B cells in Autoimmune NOD Mice," Diabetes 63(6):2051-2062 (2014).
Racine, J., et al., "MHC-Mismatched Mixed Chimerism Mediated Thymic Deletion of Cross-Reactive Autoreactive T Cells and Prevents Insulitis in Nonobese Diabetic Mice," J. Immunol. 194:407-417 (2015).
Reddy, J., et al., "Cutting Edge: CD4+ CD25+ Regulatory T Cells Contribute to Gender Differences in Susceptibility to Experimental Autoimmune Encephalomyelitis," J. Immunol. 175:5591-5595 (2005).
Rescan, C., et al., "EGF-Induced Proliferation of Adult Human Pancreatic Duct Cells is Mediated by the MEK/ERK Cascade," Lab. Invest. 85:65-74 (2005).
Rooman, I., et al., "Combined Gastrin and Epidermal Growth Factor Treatment Induces Islet Regeneration and Restores Normoglycaemia in C57Bl6/J Mice Treated with Alloxan," Diabetologia 47:259-265 (2004).
Sakaguchi, S., et al., "Regulatory T Cells and Immune Tolerance," Cell 133:775-787 (2008).
Sauter, C., et al., "Pentostatin in Chronic Lymphocytic Leukemia," Exp. Opin. Drug Metab. Toxicol. 4(9):1217-1222 (2008).
Scandling, J. D., et al., "Induced Immune Tolerance for Kidney Transplantation," N. Engl. J. Med. 365(14):1359-1360 (2011).
Scandling, J. D., et al., "Tolerance and Withdrawal of Immunosuppressive Drugs in Patients Given Kidney and Hematopoietic Cell Transplants," Am. J. Transplant. 12(5):1133-1145 (2012).
Schmidt, D., et al., "A Mechanism for the Major Histocompatibility Complex-linked Resistance to Autoimmunity," J. Exp. Med. 186(7):1059-1075 (1997).
Shapiro, A.M. J., et al., "International Trial of the Edmonton Protocol for Islet Transplantation," N. Engl. J. Med. 355:1318-1330 (2006).
Shizuru, J. A., "The Experimental Basis for Hematopoietic Cell Transplantation for Autoimmune Diseases," Thomas' Hematopoietic Cell Transplantation, Third Edition, Edited by K. G. Blume, et al., Blackwell Publishing Ltd., Chapter 25, pp. 324-343 (2007).
Smukler, S. R., et al., "The Adult Mouse and Human Pancreas Contain Rare Multipotent Stem Cells that Express Insulin," Cell Stem Cell 8:281-293 (2011).
Solar, M., et al., "Pancreatic Exocrine Duct Cells Give Rise to Insulin-Producing B Cells during Embryogenesis but Not after Birth," Developmental Cell 17:849-860 (2009).
Sospedra, M., et al., "Immunology of Multiple Sclerosis," Annu. Rev. Immunol. 23:683-747 (2005).
Steinman, L., "Immunology of Relapse and Remission in Multiple Sclerosis," Annu. Rev. Immunol. 32:257-281 (2014).
Suarez-Pinzon, W. L., et al., "Combination Therapy With Epidermal Growth Factor and Gastrin Increases β-Cell Mass and Reverses Hyperglycemia in Diabetic NOD Mice," Diabetes 54:2596-2601 (2005).
Suarez-Pinzon, W. L., et al., "Combination Therapy With Epidermal Growth Factor and Gastrin Induces Neogenesis of Human Islet β-Cells from Pancreatic Duct Cells and an Increase in Functional β-Cell Mass," J. Clin. Endocrinol. Metab. 90(6):3401-3409 (2005).
Sykes, M., et al., "Treatment of Severe Autoimmune Disease by Stem-Cell Transplantation," Nature 435:620-627 (2005).
Thorel, F., et al., "Conversion of Adult Pancreatic α-Cells to β-Cells After Extreme β-Cell Loss," Nature 464(7292):1149-1154 (2010).
Trapp, B. D., et al., "Multiple Sclerosis: An Immune or Neurodegenerative Disorder?" Annu. Rev. Neurosci. 31:247-269 (2008).
United States Patent and Trademark Office, International Search Report and Written Opinion dated Dec. 30, 2016 for PCT/US2016/061382.
United States Patent and Trademark Office, International Search Report and Written Opinion dated Dec. 31, 2016 for PCT/US2016/061403.

(56) References Cited

OTHER PUBLICATIONS

Viglietta, V., et al., "Loss of Functional Suppression by CD4+ CD25+ Regulatory T Cells in Patients with Multiple Sclerosis," J. Exp. Med. 199(7):971-979 (2004).
Wang, M., et al., "Mixed Chimerism and Growth Factors Augment β Cell Regeneration and Reverse Late-Stage Type 1 Diabetes," Science Translation Medicine 4(133):133ra59 (2012).
Wang, M., et al., "MHC-Mismatched Chimerism is Required for Induction of Transplantation Tolerance in Autoimmune Nonobese Diabetic Recipients," J. Immunol. 193:000-000 (2014) doi:10.4049/jimmunol.1401137.
Wang, Z., et al., "Role of IFN-γ in Induction of Foxp3 and Conversion of CD4+CD25− T Cells to CD4+ Tregs," J. Clin. Invest. 116(9):2434-2441 (2006).
Weir, G. C. et al., "Islet β-Cell Mass in Diabetes and How it Relates to Function, Birth, and Death," Ann. N.Y. Acad. Sci. 1281:92-105 (2013).
Weir, G. C. et al., "β-Cell Differentiation in Diabetes is Important, But What is It?" Islets 5(5):233-237 (2013).
Wu, T., et al., "Thymic Damage, Impaired Negative Selection, and Development of Chronic Graft-versus-Host Disease Caused by Donor CD4+ and CD8+ T Cells," J. Immunol. 191(1):488-499 (2013).
Wu, L., et al., "MHC-Mismatched Mixed Chimerism Augments Thymic Regulatory T-Cell Production and Prevents Relapse of EAE in Mice," PNAS 112(52):15994-15999 (2015).
Xu, X., et al., "β Cells Can Be Generated from Endogenous Progenitors in Injured Adult Mouse Pancreas," Cell 132:197-207 (2008).
Yamada, T., et al., "Reprogramming Mouse Cells With a Pancreatic Duct Phenotype to Insulin-Producing β-Like Cells," Endocrinol. 156:2029-2038 (2015).
Zhang, C., et al., "Induction of Chimerism Permits Low-Dose Islet Grafts in the Liver or Pancreas to Reverse Refractory Autoimmune Diabetes," Diabetes 59:2228-2236 (2010).
Zhang, C., et al., "Elimination of Insulitis and Augmentation of Islet β Cell Regeneration Via Induction of Chimerism in Overtly Diabetic NOD Mice," Proc. Natl. Acad. Sci. 104(7):2337-2342 (2007).
Zhou, Q., et al., "In Vivo Reprogramming of Adult Pancreatic Exocrine Cells to β-Cells," Nature 455:627-633 (2008).
Zozulya, A. L., et al., "The Role of Regulatory T Cells in Multiple Sclerosis," Neurology 4(7):384-398 (2008).
Zulewski, H., et al., "Multipotential Nestin-Positive Stem Cells Isolated From Adult Pancreatic Islets Differentiate Ex Vivo Into Pancreatic Endocrine, Exocrine, and Hepatic Phenotypes," Diabetes 50:521-533 (2001).
USPTO, Non-Final Office Action for U.S. Appl. No. 16/067,605, dated Feb. 6, 2023, 5 pages.

\* cited by examiner

Fig. 1A
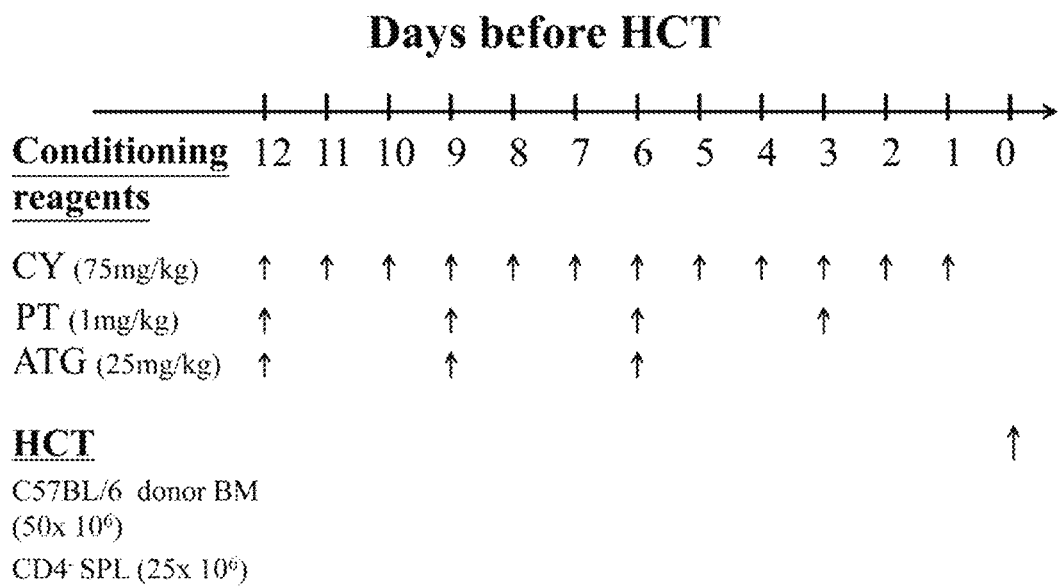
Fig. 1B
| Conditioning Regimen | Frequency of mixed chimerism by 75 days after HCT |
|---|---|
| CY+PT | 0/6 |
| CY+ATG | 0/6 |
| CY+PT+ATG | 25/35 |
| | (6 full, 1 non-engraftment, 3 loss) |
Fig. 1C
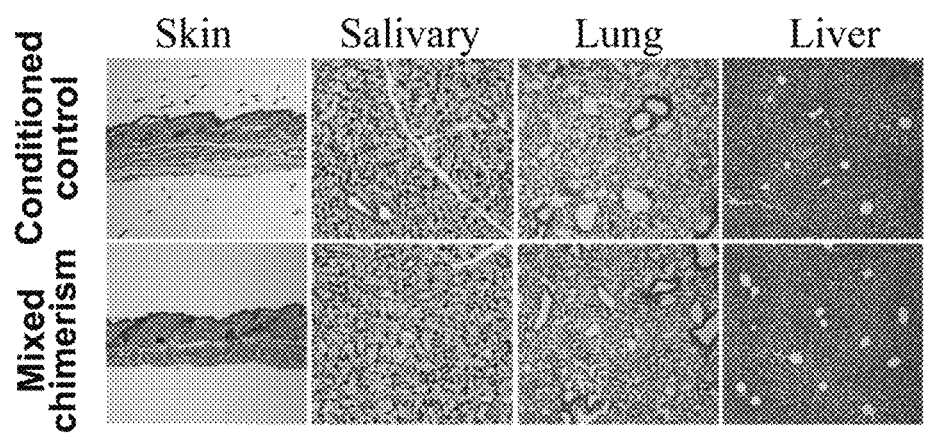

Fig. 9A
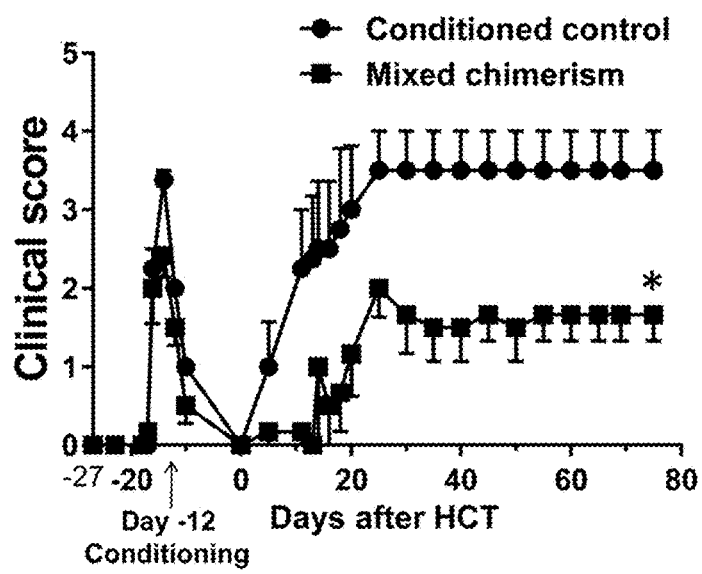
Fig. 9B
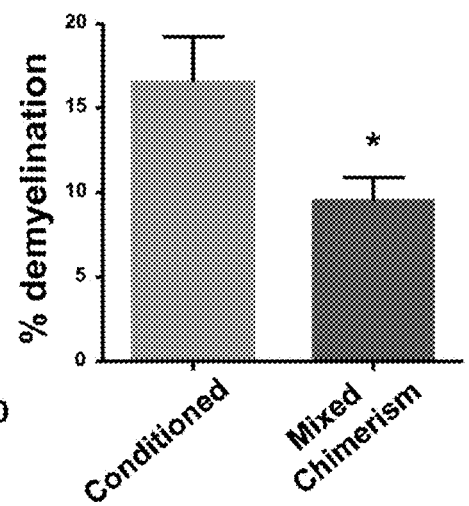
Fig. 9C
Fig. 9D
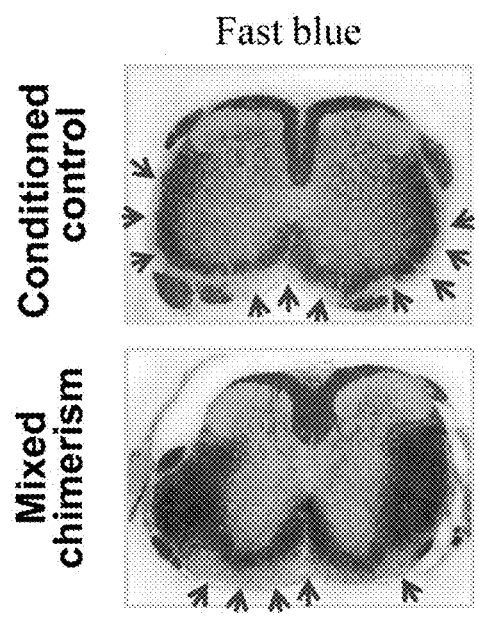
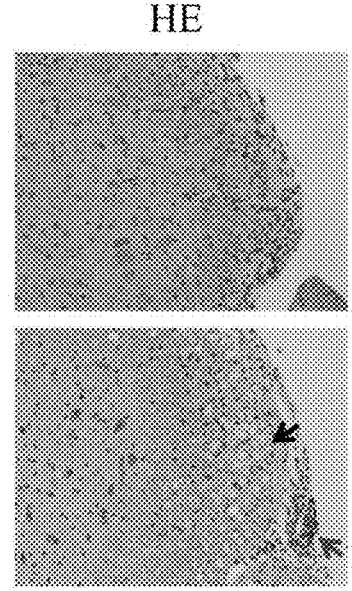

Fig. 12A

| Conditioning regimen | Days during treatment | | | | | | | | | | | | |
|---|---|---|---|---|---|---|---|---|---|---|---|---|---|
| | -12 | -11 | -10 | -9 | -8 | -7 | -6 | -5 | -4 | -3 | -2 | -1 | 0 |
| Cyc (50mg/Kg) | ↑ | ↑ | ↑ | ↑ | ↑ | ↑ | ↑ | ↑ | ↑ | ↑ | ↑ | ↑ | |
| Pen (1mg/Kg) | ↑ | | | ↑ | | | ↑ | | | ↑ | | | |
| ATG (25mg/Kg) | ↑ | | | ↑ | | | ↑ | | | | | | |
| HCT | C57BL/6 Donor, BM (50x10$^6$), CD4$^-$ spleen cells (25x10$^6$) | | | | | | | | | | | | ↑ |

Fig. 12B

| Conditioning regimen | Frequency of chimerism | | |
|---|---|---|---|
| | Complete | Mixed | None |
| Cyc + Pen + ATG | 30% (21/69) | 54% (37/69) | 16% (11/69) |

CONDITIONING REGIMENS AND METHODS FOR INDUCING MIXED CHIMERISM

PRIORITY CLAIM

This application is a continuation of U.S. application Ser. No. 15/775,358, filed May 10, 2018, and issued as U.S. Pat. No. 11,116,777 on Sep. 14, 2021, which is a U.S. National Phase Application of International Patent Application No. PCT/US2016/061382, filed Nov. 10, 2016, which claims priority to U.S. Provisional Application No. 62/253,657, filed Nov. 10, 2015, which is incorporated by reference herein in its entirety, including drawings.

BACKGROUND

Donor hematopoietic stem cell engraftment in a recipient is called chimerism. When the donor hematopoietic system totally replaces the recipient one, it is called complete chimerism, which is usually associated with graft versus host disease (GVHD). When the donor and host system co-exist, it is called mixed chimerism, which usually does not cause GVHD. Induction of stable mixed chimerism in humans is still challenging, although induction of complete chimerism is routine for classical allogeneic hematopoietic cell transplantation (HCT).

Induction of stable mixed chimerism with human leukocyte antigen (HLA)-matched donors in humans has been reported. HLA-matched stable mixed chimerism can provide organ transplantation immune tolerance without causing any signs of GVHD in non-autoimmune recipients. Total lymphoid irradiation (TLI) conditioning regimen has been used for induction of stable mixed chimerism in HLA-matched human recipients, but it has not been reported in HLA-mismatched autoimmune recipients. TLI-based conditioning regimen also is associated with undesirable side effects and is not easily acceptable for autoimmune patients. Accordingly, there remains a need to develop an effective radiation-free conditioning method to induce stable mixed chimerism, including MHC- or HLA-matched and mismatched stable mixed chimerism.

SUMMARY

In one embodiment, the disclosure provided herein relates to a conditioning regimen for inducing mixed chimerism in a subject comprising administration of radiation-free, low doses of cyclophosphamide (CY), pentostatin (PT), and anti-thymocyte globulin (ATG). The conditioning regimen may further comprise administration of a population of conditioning cells that facilitate engraftment during HCT. For example, in addition to CY, PT and ATG, the conditioning regimen may further comprise administration of one or more populations of conditioning donor cells selected from donor $CD4^+$ T-depleted spleen cells, donor $CD8^+$ T cells, and donor Granulocyte colony-stimulating factor (G-CSF)-mobilized peripheral blood mononuclear cells. The additional population of donor cells is administered on the same day as or before the transplantation of a population of donor bone marrow cells. The conditioning regimen described above is administered in conjunction with transplantation of a population of donor bone marrow cells. In some aspects, transplantation of the population of donor bone marrow cells occurs on the same day as or after the administration of the one or more population of conditioning donor cells described above. In some embodiments, the one or more populations of conditioning donor cells, the donor bone marrow cells, or both are MHC- or HLA-matched. In preferred embodiments, the one or more populations of conditioning donor cells, the donor bone marrow cells, or both are MHC- or HLA-mismatched. In some embodiments, the mixed chimerism is MHC- or HLA-matched mixed chimerism. In preferred embodiments, the mixed chimerism is MHC- or HLA-mismatched mixed chimerism.

In another embodiment, a conditioning regimen for inducing mixed chimerism in a subject comprises administration of radiation-free, low doses of cyclophosphamide (CY), pentostatin (PT), and anti-thymocyte globulin (ATG). The conditioning regimen may be administered prior to transplantation of a population of donor bone marrow cells, wherein the population of donor bone marrow cells is a population of CD4+ T-depleted bone marrow cells. In this embodiment, the conditioning regimen may optionally comprise administration of one or more population of conditioning donor cells selected from donor $CD4^+$ T-depleted spleen cells, donor $CD8^+$ T cells, and donor Granulocyte colony-stimulating factor (G-CSF)-mobilized peripheral blood mononuclear cells.

In another embodiment, the disclosure provided herein relates to a method of inducing stable mixed chimerism in a recipient by administration of radiation-free, low doses of CY, PT and ATG, followed by transplantation of $CD4^+$ T-depleted bone marrow cells. In an alternative embodiment, mixed chimerism in a recipient is induced by administration of radiation-free, low doses of CY, PT and ATG, administration of a therapeutically effective amount of donor bone marrow cells, and administration of a therapeutically effective amount of one or more populations of conditioning donor cells selected from donor $CD4^+$ T-depleted spleen cells, donor $CD8^+$ T cells, and donor G-CSF-mobilized peripheral blood mononuclear cells. In some embodiments, the one or more populations of conditioning donor cells, the donor bone marrow cells, or both are MHC- or HLA-matched with the recipient. In preferred embodiments, the one or more populations of conditioning donor cells, the donor bone marrow cells, or both are MHC- or HLA-mismatched with the recipient. In some embodiments, the mixed chimerism is MHC- or HLA-matched mixed chimerism. In preferred embodiments, the mixed chimerism is MHC-or HLA-mismatched mixed chimerism.

In another aspect, the disclosure provided herein relates to a method of conditioning a recipient for bone marrow, tissue, or organ transplantation by administration of radiation-free, low doses of CY, PT and ATG to the recipient.

In another aspect, the disclosure provided herein relates to a method of promoting transplantation immune tolerance by administration of radiation-free, low doses of CY, PT and ATG to a recipient of the transplantation. The transplantation may be tissue transplantation, bone marrow transplantation, or organ transplantation.

In another aspect, the disclosure provided herein relates to a method of treating or preventing a hereditary hematological disease or an autoimmune disease in a subject by administration of radiation-free, low doses of CY, PT and ATG to the subject followed by administering a population of bone marrow cells and one or more populations of conditioning donor cells selected from donor $CD4^+$ T-depleted spleen cells, donor $CD8^+$ T cells, and donor G-CSF-mobilized peripheral blood mononuclear cells. In some embodiments, the doses of CY, PT and ATG may be administered to a subject followed by a transplantation of donor $CD4^+$ T-depleted bone marrow cells.

Exemplary autoimmune diseases that may be treated or prevented by the methods above include, but are not limited to, multiple sclerosis, type-1 diabetes, systemic lupus, scleroderma, and chronic graft versus host disease. Exemplary hereditary hematological diseases include, but are not limited to, sickle cell disease, Thalassemia major, aplastic anemia, etc. In some embodiments, the one or more populations of conditioning donor cells, the donor bone marrow cells, or both are MHC- or HLA-matched with the recipient. In preferred embodiments, the one or more populations of conditioning donor cells, the donor bone marrow cells, or both are MHC- or HLA-mismatched with the recipient. In some embodiments, the mixed chimerism is MHC- or HLA-matched mixed chimerism. In preferred embodiments, the mixed chimerism is MHC- or HLA-mismatched mixed chimerism.

BRIEF DESCRIPTION OF THE DRAWINGS

FIGS. 1A-1C show that conditioning with low-dose CY, PT, and ATG induced mixed chimerism without causing signs of GVHD in experimental autoimmune encephalomyelitis (EAE) mice. EAE mice were conditioned by injection of CY, PT, and ATG for 12 days, and then on day 0, transplanted with donor bone marrow (BM) and $CD4^+$ T-depleted spleen cells. The recipients were monitored for mixed chimerism and clinical GVHD. FIG. 1A shows a summary of conditioning and HCT procedures. Control mice were conditioned with CY+PT or CY+ATG only. FIG. 1B shows a summary of mixed chimerism frequency under different conditioning. FIG. 1C shows representative H&E histopathology micrographs of skin, salivary gland, lung, and liver (original magnification 20×; N=6). Control mice were given conditioning only.

FIG. 3A shows kinetics of clinical score (Mean±SE). FIG. 3B shows percentage of demyelinated area in spinal cord tissues, as determined by fast blue staining at 75 days after HCT. Mean±SE of 6 replicate experiments is shown. FIG. 3C shows representative micrographs (N=6) of spinal cord tissues with fast blue staining, with arrows pointing at demyelination areas. FIG. 3D shows representative micrographs (N=6) of transmitting electronic microscopy (TEM) of spinal cord tissues. Black arrows point at demyelinated axon areas; white arrows point at remnants of damaged axons.

FIG. 4A shows that the percentage of dividing $CD4^+$ T cells was measured by flow cytometry; Mean±SE of 4 replicate experiments is shown. FIG. 4B shows representative micrograph of HE histopathology of 6 replicate experiments. FIG. 4C shows that spinal cord tissues were stained for collagen I, $CD3^+$ T and $B220^+$ B cells; the merged micrographs show ectopic lymphoid structures in the control EAE mice and elimination of the structures in the mixed chimeras. One representative micrograph is shown of 4 replicate experiments. FIG. 4D shows that spinal cord tissue infiltrating cells were analyzed for percentage of $TCR\beta^+CD4^+$ T, $B220^+$ B, and $CD11b^+F4/80^+$ macrophage cells. One representative flow cytometry pattern is shown of 6 replicate experiments. Mean±SE of $CD4^+$ T, $B220^+$ B, and $CD11b^+F4/80^+$ is shown.

FIG. 5A shows representative flow cytometry pattern and percentage of $IL-17^+$, $IFN-\gamma^+$ $CD4^+$ T cells in spleen and LN. FIG. 5B shows representative flow cytometry pattern and percentage of $Foxp3^+CD4^+$ T cells in spleen and LN. FIG. 5C shows representative flow cytometry pattern and the percentage of $Foxp3^+CD4^+$ and $Foxp3^+CD4^+CD8^+$ T cells in the thymus. The arrows indicate the gating strategy.

FIGS. 9A-9D show that induction of mixed chimerism did not prevent EAE relapse but reduced disease severity in thymectomized recipients. Thymectomized SJL/J mice were induced to develop EAE and subsequently induced to develop mixed chimerism as described in FIGS. 3A-3D. FIG. 9A shows kinetics of clinical score (Mean±SE, n=8). FIG. 9B shows percentage of demyelinated area in spinal cord tissues, as determined by fast blue staining at 75 days after HCT. Mean±SE of 4 replicate experiments is shown. FIG. 9C shows representative micrographs (N=4) of spinal cord tissues in fast blue staining, with arrows pointing at demyelination area. FIG. 9D shows the representative micrograph (N=4) of HE histopathology of spinal cord tissues. The arrow points at submembrane infiltration; the black arrow points at holes of damages axons.

FIG. 10A shows one representative flow cytometry pattern of 4 replicate experiments. Mean±SE of 4 replicate experiments is shown. FIG. 10B shows representative flow cytometry pattern and percentage of Foxp3$^+$ CD4$^+$ T cells in LN.

FIG. 11A shows kinetics of clinical score (Mean±SE, N=8). FIG. 11B shows percentage of demyelinated area in spinal cord tissues, as determined by fast blue staining at 75 days after HCT. Mean±SE of 8 replicate experiments is shown. FIG. 11C shows representative micrographs (N=8) of spinal cord tissues in fast blue staining, with arrows pointing at demyelination area. FIG. 11D shows representative micrograph (N=8) of HE histopathology of spinal cord tissues.

FIGS. 12A-12B show that conditioning with low-dose CY, PT, and ATG induced stable mixed chimerism in late-stage diabetic NOD mice. Late-stage diabetic NOD mice were conditioned by injection of CY, PT, and ATG for 12 days, and then on day 0, transplanted with donor bone marrow (BM) and CD4$^+$ T-depleted spleen cells. The recipients were monitored for mixed chimerism. FIG. 12A shows a summary of conditioning regimen and HCT procedures for diabetic NOD mice. FIG. 12B shows a summary of chimerism frequency under CY, PT, and ATG conditioning represented by the percentage of chimeric NOD mice.

DETAILED DESCRIPTION

Figure 2A:
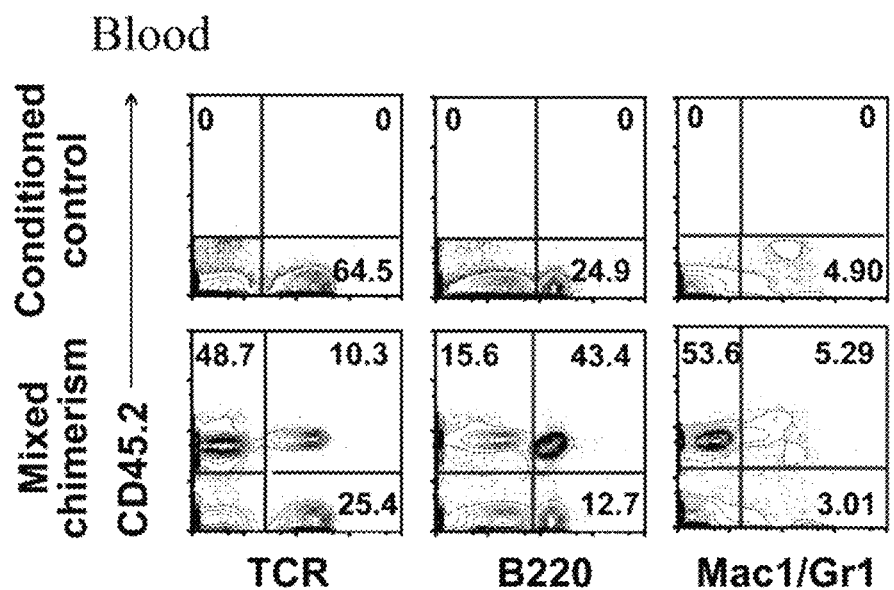
FIGS. 2A-2D show representative patterns of mixed chimerism. 75 days after HCT, mononuclear cells from blood (FIG. 2A), spleen (FIG. 2B), thymus (FIG. 2C), and bone marrow (FIG. 2D) of mixed chimeras and control mice given conditioning only were analyzed for the percentage of donor-type ($CD45.2^+$) and host-type ($CD45.1^+$) cells among T cells ($TCR\beta^+$), B cells ($B220^+$), and myeloid cells ($Mac-1^+/Gr-1^+$). One representative is shown of six replicate experiments.
Figure 2B:
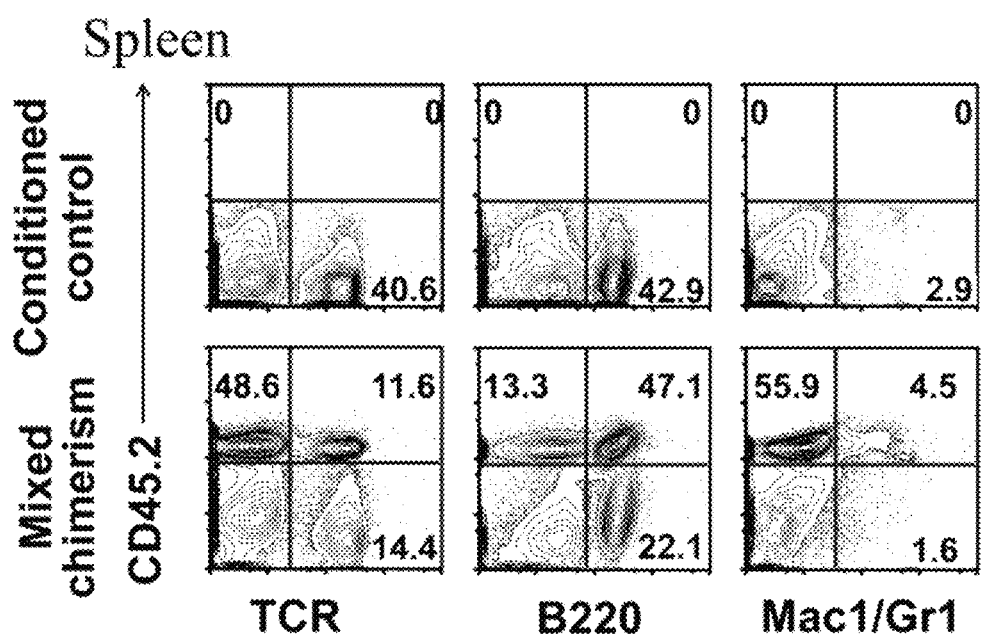
Figure 2C:
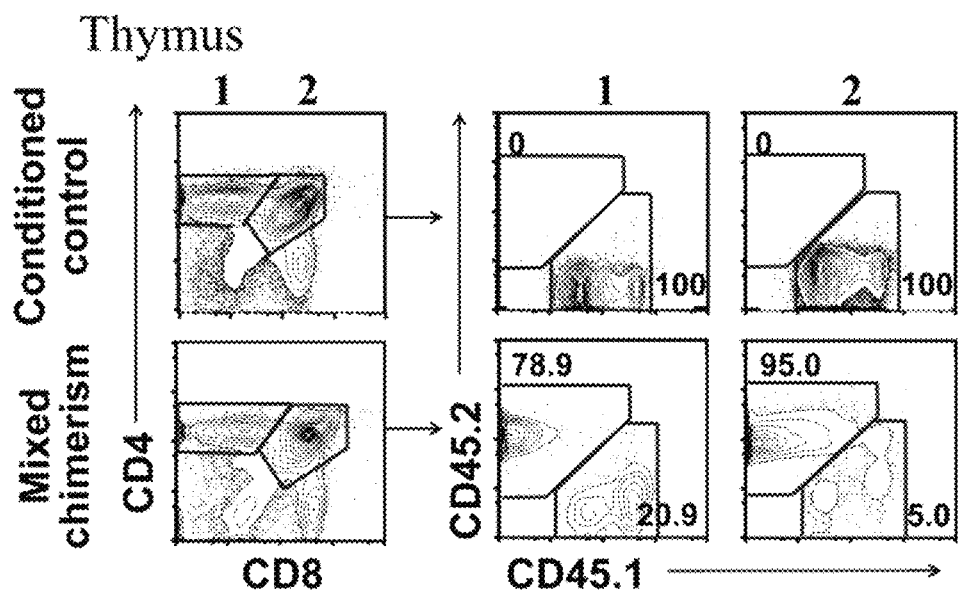
Figure 2D:
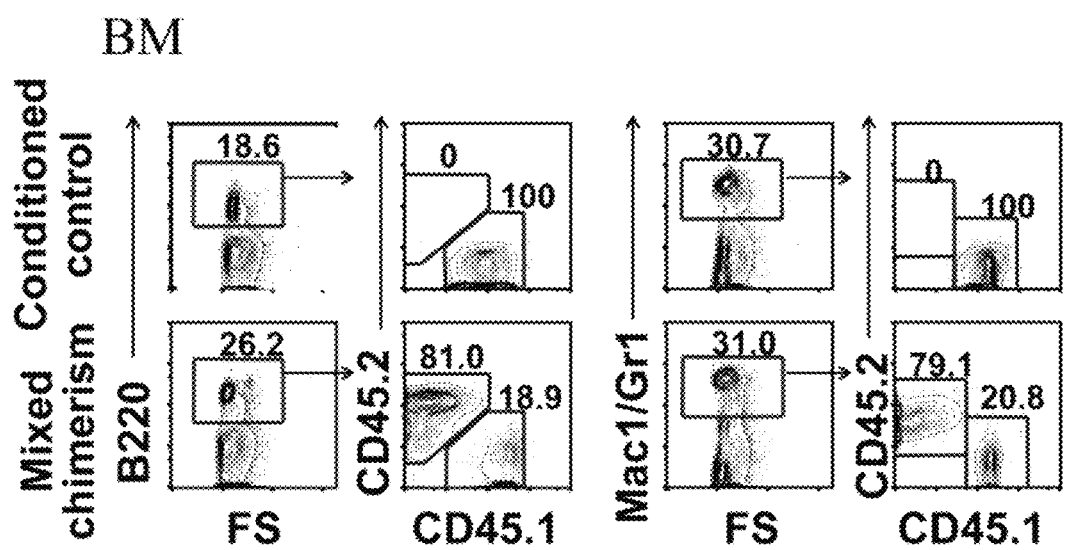

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Disclosed herein are various conditioning regimens for use in methods for establishing stable mixed chimerism without inducing GVHD. According to the embodiments described herein, a conditioning regimen for use in the methods described herein includes one or more doses of cyclophosphamide (CY), pentostatin (PT), and anti-thymocyte globulin (ATG), administered individually or in combination to condition a recipient in preparation for and prior to transplantation of donor bone marrow cells.

The conditioning regimens described herein may further comprise administration of a population of donor conditioning cells that facilitate engraftment during HCT. The population of conditioning cells may include, but are not limited to, one or more of sorted donor CD8$^+$ T cells, CD4$^+$ T-depleted spleen cells and G-CSF-mobilized peripheral blood mononuclear cells. The population of donor conditioning cells may be administered on a day prior to an HCT procedure, or may be administered on the same day as the transplantation of donor bone marrow cells.

In some embodiments, the donor bone marrow cells may be a native population of bone marrow cells, while in other embodiments, the donor bone marrow cells may be a population of CD4$^+$ T-depleted bone marrow cells. In embodiments where the donor bone marrow cells are a population of CD4$^+$ T-depleted bone marrow cells, the conditioning regimen may optionally include administration of a population of conditioning cells, such as those described above.

In some embodiments, the donor conditioning cells, the donor bone marrow cells, or both may be HLA- or MHC-matched.

In other embodiments, the donor conditioning cells, the donor bone marrow cells, or both may be HLA- or MHC-mismatched. Recent studies indicate that induction of MHC-mismatched mixed chimerism may play an important role in the therapy of autoimmune diseases and conditions as well as in organ transplantation immune tolerance. Thus, according to certain embodiments described herein, an HLA- or MHC-mismatched or haploidentical donor may be desirable to avoid disease susceptible loci.

As detailed in this disclosure, EAE SJL/J mice conditioned with a combination of low-dose CY, PT, and ATG and then transplanted with CD4$^+$ T-depleted spleen cells and bone marrow cells from MHC-mismatched C57BL/6 donors induced stable mixed chimerism. Induction of MHC-mismatched mixed chimerism is able to eliminate spinal cord tissue infiltration and augment regeneration of myelin sheath and cure acute phase EAE. Surprisingly, induction of MHC-mismatched mixed chimerism not only augments thymic deletion of host-type CD4$^+$CD8$^+$ thymocytes but also dramatically increases the percentage of Foxp3$^+$ Treg cells among the host-type CD4$^+$CD8$^+$ thymocytes. Moreover, induction of MHC-mismatched mixed chimerism is not able to prevent EAE relapse in thymectomized recipients, even though there is expansion of host-type Treg cells in the periphery.

The term "recipient" or "host" as used herein refers to a subject receiving transplanted or grafted tissue or cells. These terms may refer to, for example, a subject receiving an administration of donor bone marrow, donor T cells, or a tissue graft. The transplanted tissue may be derived from a syngeneic or allogeneic donor. The recipient, host, or subject can be an animal, a mammal, or a human.

The term "donor" as used herein refers to a subject from whom tissue or cells are obtained to be transplanted or grafted into a recipient or host. For example, a donor may be a subject from whom bone marrow, T cells, or other tissue to be administered to a recipient or host is derived. The donor or subject can be an animal, a mammal, or a human. In certain embodiments, the donor may be an MHC- or HLA-matched donor, meaning the donor shares the same MHC- or HLA with the recipient. In certain embodiments, the donor may be MHC- or HLA-mismatched to the recipient.

The term "chimerism" as used herein refers to a state in which one or more cells from a donor are present and functioning in a recipient or host. Recipient tissue exhibiting "chimerism" may contain donor cells only (complete chimerism), or it may contain both donor and host cells (mixed chimerism). "Chimerism" as used herein may refer to either transient or stable chimerism. In some embodiments, the mixed chimerism may be MHC- or HLA-matched mixed chimerism. In certain embodiments, the mixed chimerism may be MHC- or HLA-mismatched mixed chimerism.

The phrase "therapeutically effective amount" as used herein refers to an amount of an agent, population of cells, or composition that produces a desired therapeutic effect. For example, a therapeutically effective amount of donor BM cells or donor $CD4^+$ T-depleted spleen cells may refer to that amount that generates chimerism in a recipient. The precise therapeutically effective amount is an amount of the agent, population of cells, or composition that will yield the most effective results in terms of efficacy in a given subject. This amount will vary depending upon a variety of factors, including but not limited to the characteristics of the therapeutic agent, population of cells, or composition (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of an agent, population of cells, or composition and adjusting the dosage accordingly. For additional guidance, see Remington: The Science and Practice of Pharmacy (Gennaro ed. $20^{th}$ edition, Williams & Wilkins PA, USA) (2000).

According to some embodiments, the agents and/or cells administered to a recipient may be part of a pharmaceutical composition. Such a pharmaceutical composition may include one or more of CY, PT and ATG and a pharmaceutically acceptable carrier; or one or more populations of donor cells and a pharmaceutically acceptable carrier. The pharmaceutical compositions described herein may include compositions including a single agent or a single type of donor cell (e.g., donor bone marrow cells, donor $CD4^+$ T-depleted spleen cells, donor $CD8^+$ T cells, or donor G-CSF-mobilized peripheral blood mononuclear cells) in each composition, or alternatively, may include a combination of agents, populations of cells, or both.

A "pharmaceutically acceptable carrier" as used herein refers to a pharmaceutically acceptable material, composition, or vehicle that is involved in carrying or transporting an agent or cell of interest from one tissue, organ, or portion of the body to another tissue, organ, or portion of the body. Such a carrier may comprise, for example, a liquid, solid, or semi-solid filler, solvent, surfactant, diluent, excipient, adjuvant, binder, buffer, dissolution aid, solvent, encapsulating material, sequestering agent, dispersing agent, preservative, lubricant, disintegrant, thickener, emulsifier, antimicrobial agent, antioxidant, stabilizing agent, coloring agent, or some combination thereof. Each component of the carrier is "pharmaceutically acceptable" in that it must be compatible with the other ingredients of the composition and must be suitable for contact with any tissue, organ, or portion of the body that it may encounter, meaning that it must not carry a risk of toxicity, irritation, allergic response, immunogenicity, or any other complication that excessively outweighs its therapeutic benefits.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) natural polymers such as gelatin, collagen, fibrin, fibrinogen, laminin, decorin, hyaluronan, alginate and chitosan; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as trimethylene carbonate, ethyl oleate and ethyl laurate; (13) agar; (14) buffering agents, such as magnesium hydroxide and aluminum hydroxide; (15) alginic acid (or alginate); (16) pyrogen-free water; (17) isotonic saline; (18) Ringer's solution; (19) alcohol, such as ethyl alcohol and propane alcohol; (20) phosphate buffer solutions; (21) thermoplastics, such as polylactic acid, polyglycolic acid, (22) polyesters, such as polycaprolactone; (23) self-assembling peptides; and (24) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The term "low dose" as used herein refers to a dose of a particular agent, such as cyclophosphamide (CY), pentostatin (PT), or anti-thymocyte globulin (ATG), and is lower than a conventional dose of each agent used in a conditioning regimen, particularly in a myeloablative conditioning regimen. For example, the dose may be about 5%, about 10%, about 15%, about 20% or about 30% lower than the standard dose for conditioning. In certain embodiments, a low dose of CY may be from about 30 mg/kg to about 75 mg/kg; a low dose of PT is about 1 mg/kg; and a low dose of ATG may be from about 25 mg/kg to about 50 mg/kg. In general, different animals require different doses and human doses are much lower than mouse doses. For example, a low dose for BALB/c mice is about 30 mg/kg, for C57BL/6 mice is from about 50 mg/kg to about 75 mg/kg or from about 50 mg/kg to about 100 mg/kg, and for NOD mice is about 40 mg/kg.

In some embodiments, the human dose of CY used in the conditioning regimens and methods described herein may be from about 50 mg to about 1000 mg, from about 100 mg to about 800 mg, from about 150 mg to about 750 mg, from about 200 mg to about 500 mg, about 100 mg, about 200 mg, about 300 mg, about 400 mg, about 500 mg, about 600 mg, about 700 mg, or about 800 mg. In some embodiments, the human dose of ATG used in the conditioning regimens and methods described herein may be from about 0.5 mg/kg/day to about 10 mg/kg/day, from about 1.0 mg/kg/day to about 8.0 mg/kg/day, from about 1.5 mg/kg/day to about 7.5 mg/kg/day, from about 2.0 mg/kg/day to about 5.0 mg/kg/day, about 0.5 mg/kg/day, about 1.0 mg/kg/day, about 1.5 mg/kg/day, about 2.0 mg/kg/day, about 2.5 mg/kg/day, about 3.0 mg/kg/day, about 3.5 mg/kg/day, about 4.0 mg/kg/day, about 4.5 mg/kg/day, or about 5.0 mg/kg/day. In some embodiments, the human dose of PT used in the conditioning regimens and methods described herein may be from about 1 $mg/m^2$/dose to about 10 $mg/m^2$/dose, from about 2 $mg/m^2$/dose to about 8 $mg/m^2$/dose, from about 3 $mg/m^2$/dose to about 5 $mg/m^2$/dose, about 1 $mg/m^2$/dose, about 2 $mg/m^2$/dose, about 3 $mg/m^2$/dose, about 4 $mg/m^2$/dose, about 5 mg/m²/dose, about 6 mg/m²/dose, about 7 mg/m²/dose, about 8 mg/m²/dose, about 9 mg/m²/dose, or about 10 mg/m²/dose.

In another aspect, the conditioning regimens and methods described herein include administering the CY, PT, and/or ATG on a daily, weekly, or other regular schedule. For example, administration of CY may be daily; administration of PT may be weekly or at a interval greater than every day (e.g., every two or three days); and administration of ATG may be daily, weekly, or at a interval greater than every day (e.g., every two or three days).

In certain embodiments, a dose of CY may be administered to the recipient on a daily basis for up to about 28 days, up to about 21 days, up to about 14 days, up to about 12 days or up to about 7 days prior to transplantation. In certain embodiments, a dose of CY may be administered to the recipient every other day for up to about 28 days, up to about 21 days, up to about 14 days, or up to about 7 days prior to transplantation. In one example, a dose of CY may be administered to the recipient on a daily basis for about 21 days prior to transplantation.

In certain embodiments, a dose of PT may be administered to the recipient every day, every other day, every third day, every fourth day, every fifth day, every sixth day, or every week for up to about 28 days, up to about 21 days, up to about 14 days, up to about 12 days or up to about 7 days prior to transplantation. In one example, a dose of PT may be administered to the recipient every week for about 21 days prior to transplantation.

In certain embodiments, a dose of ATG may be administered to the recipient every other day, every third day, every fourth day or every fifth day for up to about 28 days, up to about 21 days, up to about 14 days, up to about 12 days or up to about 7 days prior to transplantation. For example, a dose of ATG may be administered to the recipient every third day for about 21 days prior to transplantation. In certain embodiments, a dose of ATG may be administered for two, three, or four days in a row about one 7 days, 8 days, 9 days, 10 days, 11 days, 12 days, 13 days, or 14 days prior to transplantation.

In one embodiment, the conditioning regimen includes (i) three doses of PT at a dose of about 4 mg/m²/dose may be administered to a human patient about 3 weeks, about 2 weeks and about 1 week before transplantation; (ii) three doses of ATG at a dose of about 1.5 mg/kg/day may be administered to a human patient about 12 days, about 11 days, and about 10 days before transplantation; and (iii) CY at a dose of about 200 mg orally may be administered to a human patient on a daily basis about 3 weeks before transplantation.

It is within the purview of one of ordinary skill in the art to select a suitable route of administration of CY, PT and ATG. For example, these agents can be administered by oral administration including sublingual and buccal administration, and parenteral administration including intravenous administration, intramuscular administration, and subcutaneous administration. In a preferred embodiment, one or more of CY, PT and ATG are administered intravenously. In some embodiments, CY is administered orally and ATG and PT are administered intravenously.

The depletion of CD4⁺ cells and/or the combination of CY, PT and ATG allows lowering the dose of each of CY, PT and ATG, thereby to reduce the toxic side effects while achieving mixed chimerism. It is within the purview of one of ordinary skill in the art to adjust the dose of each of CY, PT and ATG to achieve the desired effect.

Mixed chimerism may be induced by conditioning with the combination of CY, PT and ATG and supplying to the recipient donor bone marrow cells and donor CD8⁺ T cells that facilitate engraftment. In some embodiments, the methods disclosed herein may include transplantation of CD4⁺ T-depleted bone marrow cells following administration of CY, PT and ATG in accordance with the conditioning regimens described above. In some embodiments, the methods disclosed herein may include administering donor bone marrow cells, and one or more types of cells selected from CD4⁺ T-depleted spleen cells, donor CD8⁺ T cells, and donor G-CSF-mobilized peripheral blood mononuclear cells following administration of the CY, PT and ATG.

In another aspect, the disclosure provided herein relates to a method of inducing stable mixed chimerism in a recipient by administration of radiation-free, low doses of CY, PT and ATG, followed by transplantation of CD4⁺ T-depleted bone marrow cells. In certain embodiments, mixed chimerism in a recipient is induced by administration of radiation-free, low doses of CY, PT and ATG, a therapeutically effective amount of donor bone marrow cells, and a therapeutically effective amount of one or more types of cells selected from donor CD4⁺ T-depleted spleen cells, donor CD8⁺ T cells, and donor G-CSF-mobilized peripheral blood mononuclear cells. CY, PT and ATG are administered to the recipient before transplantation, in accordance with the conditioning regimen described above. In some embodiments, the donor cells are MHC- or HLA-matched. In preferred embodiments, the donor cells are MHC- or HLA-mismatched. In certain embodiments, the mixed chimerism is HLA- or MHC-mismatched mixed chimerism.

The term "simultaneously" as used herein with regards to administration of two or more agents means that the agents are administered at the same or nearly the same time. For example, two or more agents are considered to be administered "simultaneously" if they are administered via a single combined administration, two or more administrations occurring at the same time, or two or more administrations occurring in succession without extended intervals in between.

In another aspect, the disclosure provided herein relates to a method of conditioning a recipient for bone marrow, tissue, or organ transplantation by administration of low doses of CY, PT and ATG to the recipient. In certain embodiments, the low doses of CY, PT and ATG may be radiation-free. In certain embodiments, the doses of CY, PT and ATG may be administered to the recipient before the transplantation using a conditioning regimen such as that described above.

In another aspect, the disclosure provided herein relates to a method of promoting transplantation immune tolerance in a recipient by administration of radiation-free, low doses of CY, PT and ATG to the recipient before a transplantation. The transplantation may be tissue transplantation, bone marrow transplantation, or organ transplantation. In certain embodiments, the doses of CY, PT and ATG may be administered to the recipient using a conditioning regimen such as that described above.

The methods of conditioning a recipient for bone marrow, tissue, or organ transplantation described above may also include administration of one or more population of conditioning donor cells, such as those described above.

In another aspect, the disclosure provided herein relates to a method of treating or preventing a hereditary hematological disease or an autoimmune disease in a subject by administration of radiation-free, low doses of CY, PT and ATG to the subject followed by supplying to the recipient donor bone marrow cells and donor CD8⁺ T cells that facilitate engraftment. For example, the method may entail transplantation of CD4$^+$ T-depleted bone marrow cells. In certain embodiments, the method may entail the steps of administration of radiation-free low doses of CY, PT and ATG, administering a therapeutically effective amount of donor bone marrow cells, and administering a therapeutically effective amount of one or more population of conditioning donor cells, selected from donor CD4$^+$ T-depleted spleen cells, donor CD8$^+$ T cells, and donor G-CSF-mobilized peripheral blood mononuclear cells. In some embodiments CY, PT and ATG may be administered simultaneously or sequentially, before the transplantation. In other embodiments, the CY, PT, and ATG may be administered in accordance with the dosing and frequency described in the conditioning regimens above. It is within the purview of one ordinary skill in the art to adjust the administration schedule to achieve the desired therapeutic or prophylactic effects. In some embodiments, exemplary autoimmune diseases include, but are not limited to, multiple sclerosis, type-1 diabetes, systemic lupus, scleroderma, and chronic graft versus host disease. In some embodiments, exemplary hereditary hematological diseases include, but are not limited to, sickle cell disease, Thalassemia major, aplastic anemia, etc.

In some embodiments, the method of treating or preventing a hereditary hematological disease or an autoimmune disease in a subject includes a step of administering a conditioning regimen, such as those described above, followed by a step of transplanting a population of donor bone marrow cells.

The terms "treat," "treating," or "treatment" as used herein with regards to a condition refers to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Multiple sclerosis (MS) is an inflammatory autoimmune disease that attacks the central nervous system, resulting in demyelination, damage to neuronal cells, and paralysis (1-6). MS patients have quantitative and qualitative defects in peripheral Foxp3$^+$ Treg cells (7-9). Different from other autoimmune diseases, such as autoimmune type-1 diabetes and systemic lupus, MS often manifests with a progressive pattern of remission and relapse (1). Remission is associated with an increase of peripheral Treg cells in humans and an enhanced suppressive capacity of Treg cells in mouse models (10, 11). However, effective Treg therapy has not been reported (12).

Autologous hematopoietic cell transplantation (HCT) has become a highly beneficial treatment for patients with highly active, rapidly progressing MS which is refractory to conventional MS therapy (13). About 45% of HCT-treated patients have a stable EDSS score (Expanded Disability Status Scale) for 7 years (14-16). But progression-free survival is lower in studies with longer follow-up (17, 18), and the reconstituted immune system remains prone to autoimmunity (19). There are currently no clinical trials for allogeneic HCT as therapy for MS, although allogeneic HCT has been applied to MS patients with hematological malignancies (20). A retrospective analysis of these studies has shown that even HLA-matched transplantation, when done under severe myeloablative conditioning, can lead to GVHD development and worsen neurologic symptoms (21, 22). Thus, classical HCT that induces complete chimerism and GVHD is not beneficial for MS.

Induction of mixed chimerism with major histocompatibility complex (MHC)-matched allogeneic HCT, on the other hand, has been shown to provide transplantation immune tolerance without causing any signs of GVHD in humans (23). However, HLA-matched mixed chimerism was unable to reverse systemic lupus (23); whereas induction of MHC-mismatched mixed chimerism was able to reverse autoimmunity in mouse models (24-29). It was reported that induction of mixed chimerism under a radiation-free anti-CD3/CD8 conditioning regimen reversed autoimmune type 1 diabetes (T1D) and systemic lupus (30-38). Induction of MHC-mismatched mixed chimerism was able to restore central tolerance by deleting autoreactive thymocytes with cross-reactivity (37), and tolerize residual T cells in the periphery as well as delete pre-existing and immature autoreactive B cells (34, 36). Due to the lack of suitable anti-human CD3 and anti-human CD8 mAb, translation of this novel regimen has been hindered.

CY is an alkylating agent whose main effect is due to its metabolite phosphoramide mustard. This metabolite is only formed in cells that have low levels of aldehyde dehydrogenase (ALDH). Phosphoramide mustard creates nucleotide crosslinks between and within DNA strands at guanine N-7 positions, leading to cell apoptosis. Cyclophosphamide has relatively little typical chemotherapy toxicity, as ALDHs only are present in relatively large concentrations in bone marrow, liver and intestinal epithelial cells. Treg cells express higher levels of ALDH than conventional T cells. For these reasons, CY has been used in combination with radiation as part of preconditioning regimens or post-transplantation immunosuppressants in HCT and organ transplantation (42, 43).

Pentostatin (PT) is a purine analog that can result in lymphocyte toxicity by inhibiting adenosine deaminase (44). An inherited deficiency of adenosine deaminase causes a disease in which both T and B cells fail to mature (45). In the setting of hairy cell leukemia or GVHD therapy, pentostatin results in profound reduction of absolute T cell counts and relative increase of myeloid cells; this can reduce the incidence of infection associated with conditioning induced lymphocyte depletion.

Anti-thymocyte globulin (ATG) has been used in combination with total lymphoid irradiation (TLI) as a non-myeloablative conditioning regimen for HCT and induction of mixed chimerism in both animal models and humans (46, 47).

Although high-dose CY and PT has been used to condition patients with hematological malignancies as a preparation for an HLA-matched or haplo-mismatched HCT, the patients usually developed complete chimerism and GVHD. TLI and ATG conditioning causes undesirable side effects as well, such as short-term toxicity.

As described in this disclosure, it was unexpectedly discovered that using a clinically applicable conditioning regimen, induction of MHC-mismatched mixed chimerism with C57BL/6 (H-2$^b$) donor transplants was able to cure autoimmune EAE in SJL/J (H-2$^s$) recipients as well as augment myelin sheath regeneration and cure paralysis in early-stage mice whose axon had not been damaged. While not wishing to be bound by theory, the reversal of autoimmunity appears to be associated with augmentation of negative selection of host-type CD4$^+$CD8$^+$ thymocytes and increase of production of Foxp3$^+$ Treg cells among CD4$^+$CD8$^-$ and CD4$^+$CD8$^+$ thymocytes. In addition, the presence of host-thymus is required for the reversal of autoimmunity, as well as, importantly, mismatched rather than matched MHC.

In the working examples disclosed herein, it has been shown that induction of MHC-mismatched mixed chimerism with $H-2^b$ transplants is able to markedly reduce $CD4^+CD8^+$ thymocytes in autoimmune EAE but not in non-autoimmune SJL/J ($H-2^s$) mice. In addition, EAE mice or non-EAE SJL/J mice treated with conditioning alone does not show reduction of $CD4^+CD8^+$ thymocytes.

The working examples described herein further demonstrate that conditioning with low-dose CY, PT, and ATG as well as transplanting BM and $CD4^+$ T-depleting spleen cells, induces mixed chimerism in most of the recipients. Mixed chimerism does not cause GVHD, and the lack of GVHD is important for MHC-mismatched mixed chimerism to restore central tolerance; otherwise, GVHD itself damages thymic mTEC and worsens autoimmunity, as it was reported in prior publication (58).

The working examples described herein further demonstrate that induction of MHC-mismatched mixed chimerism appears to augment thymic generation of $Foxp3^+$ Treg cells. In the MHC-mismatched mixed chimeric EAE mice, the percentage of $Foxp3^+CD4^+CD8^+$ thymocytes increases by more than 20 fold as compared with non-chimeric EAE mice. It has been reported that Foxp3 expression takes place in late-stage of $CD4^+CD8^+$ thymocyte development with stimulation by medium-high affinity to self-MHC-antigen complex and that agonistic interaction with thymocyte TCR augments thymic Treg production (59).

Induction of mixed chimerism in non-autoimmune SJL/J mice does not result in reduction of $CD4^+CD8^+$ thymocytes or increase the percentage of $Foxp3^+$ cells among $CD4^+CD8^+$ thymocytes. Induction of mixed chimerism in $H-2^g$ NOD mice with $H-2^b$ donors does not increase the percentage of $Foxp3^+$ cells among $CD4^+CD8^+$ thymocytes, either. Thus, the increase of $Foxp3^+$ expression among $CD4^+CD8^+$ thymocytes in EAE mixed chimeras appears to come from TCR interaction with a particular $H-2^b$-EAE autoantigen complex.

The working examples described herein further demonstrate that induction of MHC-mismatched mixed chimerism appears unable to reverse autoimmunity in thymectomized EAE mice. The thymectomized EAE mice treated with conditioning alone has a higher percentage (about 25%) of $Foxp3^+$ Treg cells among host-type $CD4^+$ T cells as compared to about 10% in normal SJL/J mice. Induction of mixed chimerism further increases the Treg percentage to about 40%. However, either conditioning alone or induction of MHC-mismatched mixed chimerism is unable to prevent EAE relapse in the thymectomized mice. It is possible that thymectomy causes lymphopenia in which autoreactive T cells are resistant to Treg suppression. It has been observed that under a lymphopenia condition, effector T cells are resistant to induction of tolerance or Treg suppression (60). Also $Foxp3^+$ Treg cells of MS patients have been reported to have defects in both quantity and quality (8). Thus, another possibility is that host-type Treg cells from de novo-generation in the thymus of MHC-mismatched mixed chimeras may have better suppressor function.

MS is one of the most common chronic neurological diseases in young adults (61), and these patients usually have thymic function. Thus, induction of mixed chimerism can be a potential long-term cure for young, newly diagnosed MS patients. In addition, the progression of late-stage EAE is lessened although mice with paralysis does not recover after induction of mixed chimerism. Thus, this therapy can still be beneficial to late-stage patients.

Induction of mixed chimerism under the radiation-free conditioning regimen of CY, PT, and ATG with HLA- or MHC-mismatched or haplo-identical donor transplants represents a therapy for patients with hereditary hematological diseases and autoimmune diseases such as highly active, progressing MS that is refractory to conventional MS therapies, as well as for patients with organ transplantation to increase immune tolerance.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Materials and Methods

EAE induction and score: EAE was induced in 9- to 11-week-old SJL/J female mice by subcutaneous (s.q.) injection with Hook Kit™ PLP139-151/CFA emulsion followed by intraperitoneal (i.p.) injection of 500 ng of Bordetella pertussis toxin (Sigma) in phosphate-buffered saline (PBS) at the time of immunization. The classical clinical manifestation of EAE in murine models is ascending motor paralysis, beginning in the tail and leading to forelimb paralysis. Mice were examined daily for disease symptoms as described previously (48). Briefly, the mice were scored for disease severity using an EAE scoring scale of 0 for no clinical signs of disease; 1 for development of a limp tail; 2 for paraparesis with weakness or partial paralysis of 1 or 2 hind limbs; 3 for paraplegia with complete paralysis of 2 hind limbs; 4 for complete hind limb paraplegia and fore limb weakness or paralysis; and 5 for moribund.

Histology and Immunohistochemistry: Formalin fixed spinal cords were paraffin embedded and coronally sectioned (6 μm), and slides were analyzed after staining for demyelination (Luxol fast blue, LFB) and infiltration (hematoxylin and eosin, HE). For Luxol fast blue stain, slides were deparaffinized and hydrated, in a serial fashion, with solutions ranging from 70-95% ethanol, then incubated with 0.1% Solvent Blue 38 (Sigma-Aldrich, Cat. No. S3382) solution at 58° C. overnight. Excess stain was washed away with 95% ethyl alcohol and differentiated in 0.05% lithium carbonate (Sigma-Aldrich, Cat. No. 203629) solution and 95% ethyl alcohol. Slides were mounted with resinous medium after dehydration. For immunohistochemistry of the spinal cord, mice were perfused with PBS and 4% paraformaldehyde. Frozen O.C.T.-embedded spinal cord was horizontally-sectioned (10 μm). Series of sections (1 out of every 20 serial sections) were acetone-fixed, blocked in 10% normal goat serum, then incubated with Collagen Type I antibody (1:800, Rockland, Cat. No. 600-401-103-0.1), CD3εantibody (1:400, eBioscience, Cat. No. 14-0031-82) and Allophycocyanin-eFluor™ 780 B220 (CD45R) antibody (1:400, eBioscience, Cat. No. 47-0452-82) diluted in PBS/BSA overnight at 4° C., then sequentially incubated with Cy3-Donkey Anti-Rabbit IgG (Jackson ImmunoResearch, Cat. No. 711-166-152) and FITC-Anti Hamster IgG (eBioscience, Cat. No. 11-4111-85) in PBS/BSA for 2 hours at room temperature.

Transmission electron microscopy (TEM): Mice were pre-perfused with PBS followed by 2.5% (v/v) glutaraldehyde, and post-fixed with 2.5% (v/v) glutaraldehyde followed by 1% osmium tetroxide. Semi-thin sections (1.0-1.5 µm) were prepared and mounted on microscope slides and stained with toluidine blue for examining with light microscopy to locate an appropriate area for electron microscopy. The ultrathin sections of 55-65 nm were mounted on copper grids and stained with uranyl acetate and lead citrate. The stained ultrathin sections were examined on a FEI Tecnai 12 transmission electron microscope equipped with a Gatan Ultrascan 2K CCD camera.

Flow cytometry staining and analysis: Multiple-color fluorescence-activated cell sorter (FACS) analyses were performed at City of Hope FACS facility using a 3-laser CyAn immunocytometry system (Dako Cytomation, Fort Collins, CO), and data were analyzed using FlowJo software (TreeStar, San Carlos, CA). Flow cytometry staining and analysis were performed as previously described (49). The following antibodies and reagent were used for flow cytometry: F4/80-FITC (eBioscience, Cat. No. 11-4801-82), PE-CD11b (BD Pharmingen, Cat. No. 553311), AlexaFluor780-TCRb (eBioscience, Cat. No. 47-5961-82), PE-Cy7-CD4 (BD biosciences, Cat. No. 552051), Pacific Blue CD45R/B220 (BD Pharmingen, Cat. No. 558108), APC-CD11c (eBioscience, Cat. No. 17-0114), Pacific Blue-CD45.1 (eBioscience, Cat. No. 48-0453-82), FITC-CD45.2 (BD Pharmingen, Cat. No. 553772), APC-IL-17 (eBioscience, Cat. No. 17-7177-81), PE-IFN-γ (eBioscience, Cat. No. 12-7311-82), PE-CD8α (eBioscience, Cat. No. 12-0081-82), APC-Foxp3 (eBioscience, Cat. No. 17-5773), Live/dead (Invitrogen, Cat. No. L34957), Foxp3 staining Fixation/Permeabilization and permeabilization buffers (eBioscience, Cat. No. 00-5523-00).

T cell proliferation assay: $CD4^+$ T cells and $CD11c^+$ DCs were enriched by positive selection using α-CD4 magnetic beads (Miltenyi Biotec, Cat. No. 130-052-001) and αCD11c magnetic beads (Miltenyi Biotec, Cat. No. 130-052-001) on the autoMACS.Pro machine (Miltenyi Biotec), as described previously (32, 50). Purified CFSE (2.5 µM, Life Technologies, Cat. No. C34554) labeled spleen $CD4^+$ T cells ($2 \times 10^5$) together with irradiated syngeneic SJL/J CD11c DCs ($1 \times 10^5$) were cultured in a U-bottom 96-well plate for 72 hours with PLP 139-151 (20 ug/ml) in complete RPMI 1640 media containing 10% FBS, penicillin/streptomycin, I-glutamine, and 2-ME. After 72 hours, spleen cells were harvested and stained with APC-TCRβ (eBioscience, Cat. No. 17-5961-83) and PE-Cy7-CD4 (BD biosciences, Cat. No. 552051) mAbs. The percentages of $TCRβ^+CD4^+$ cells with dilution of CFSE were determined by FACS analysis.

Example 1: Radiation-Free Conditioning Regimen with CY, PT and ATG in EAE Mice

This example demonstrates that radiation-free conditioning regimen with CY, PT and ATG induced mixed chimerism without causing GVHD in EAE mice.

Based on previous publications (39) and preliminary experiments, SJL/J experimental autoimmune encephalomyelitis (EAE) ($H-2^s$) mice were conditioned and induced for mixed chimerism with a regimen consisting of clinically available reagents including CY, PT and ATG, as described in FIG. 1A. In brief, EAE mice were conditioned with i.p. injection of CY (75 mg/Kg) daily for 12 days, PT (1 mg/Kg) every 4 days for a total 4 injections, and ATG (25 mg/Kg) every 4 days for 3 injections. The recipients conditioned with CY+PT or CY+ATG were used as controls. On day 0, recipients were transplanted with bone marrow (BM) cells ($50 \times 10^6$) and $CD4^+$ T-depleted spleen cells ($25 \times 10^6$) from MHC-mismatched C57BL/6 ($H-2^b$) donors. After HCT, the recipients were monitored for clinical signs of GVHD and checked for chimerism monthly by staining peripheral blood mononuclear cells with fluorescently labeled anti-donor marker antibody (anti-$H-2^b$). It was found that none (0/6) of the recipients conditioned with CY and PT or CY and ATG alone developed chimerism, that is, no donor cell engraftment at all (FIG. 1B).

In contrast, 71% (25/35) of recipients conditioned with CY, PT, and ATG developed stable mixed chimerism, 17% (6/35) developed mixed chimerism, 8.5% (3/35) developed transient mixed chimerism, and 2.8% (1/35) had no engraftment (FIG. 1B). At the experimental endpoint (75 days after HCT), the stable mixed chimeras did not show any signs of GVHD and their tissues of skin, salivary gland, lung, and liver appeared to be the same as that of mice given conditioning alone (FIG. 1C). The mixed chimerism status was also confirmed at experimental endpoint by the co-existence of donor and host-type T, B, and myeloid cells in the blood, spleen, thymus, and bone marrow (FIGS. 2A-2D). These results indicate that conditioning with CY, PT, and ATG together were required for induction of stable mixed chimerism when transplanting bone marrow and $CD4^+$ T-depleted spleen cells from MHC-mismatched donors.

Example 2: Induction of Mixed Chimerism in EAE Mice

This example demonstrates that induction of mixed chimerism prevented EAE relapse, augmented myelin sheath regeneration and prevented axon damage.

Figure 3A:
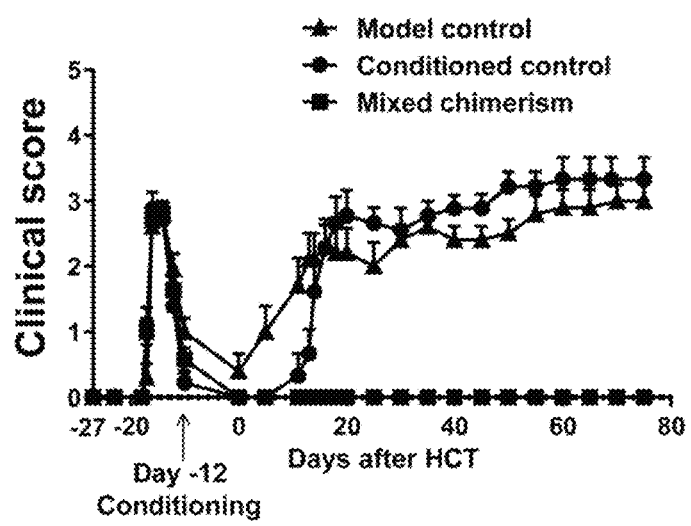
FIGS. 3A-3D show that induction of MHC-mismatched mixed chimerism prevented EAE relapse, augmented myelin regeneration and prevented axon damage. EAE mice were conditioned with CY, PT, and ATG at their first remission period as indicated by the arrow in Panel A, and transplanted with BM and $CD4^+$ T-depleted spleen cells from MHC-mismatched C57BL/6 donors to induce mixed chimerism (N=25). As a control, EAE mice were either treated with PBS (N=12) or given conditioning only (N=12).
Figure 3B:
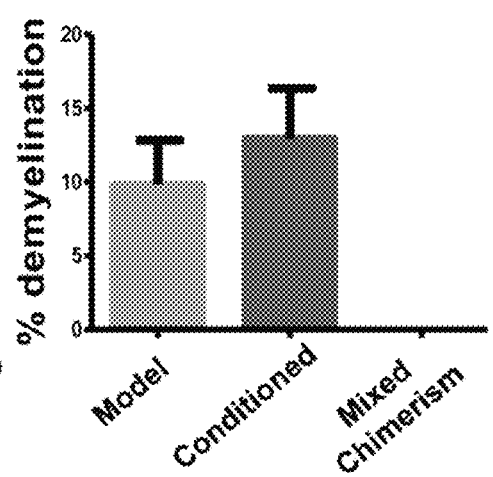
Figure 3C:
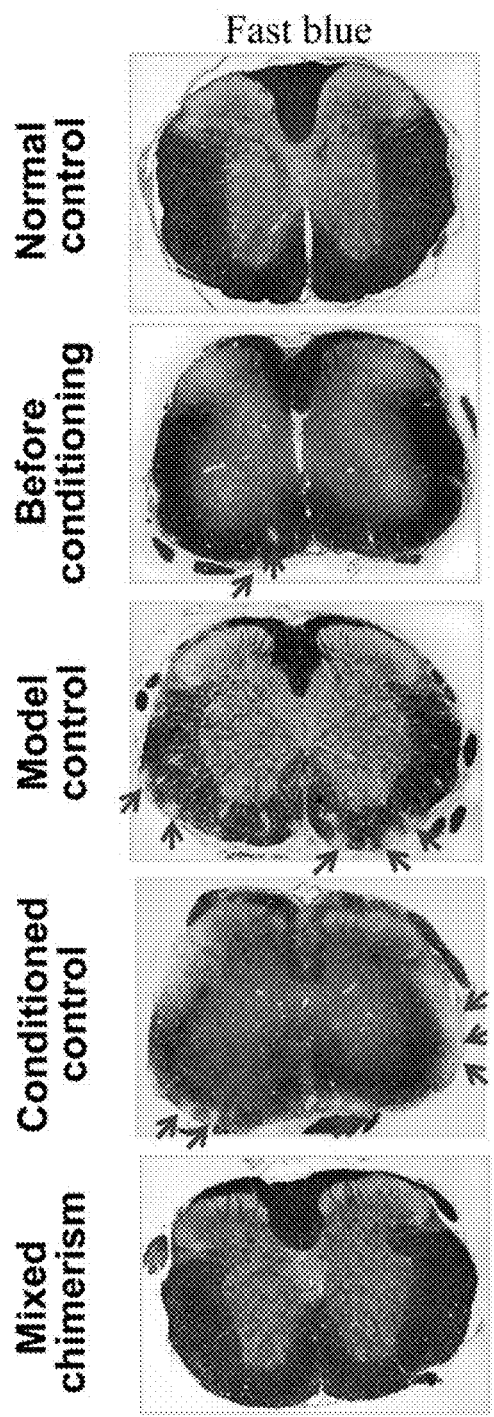
Figure 3D:
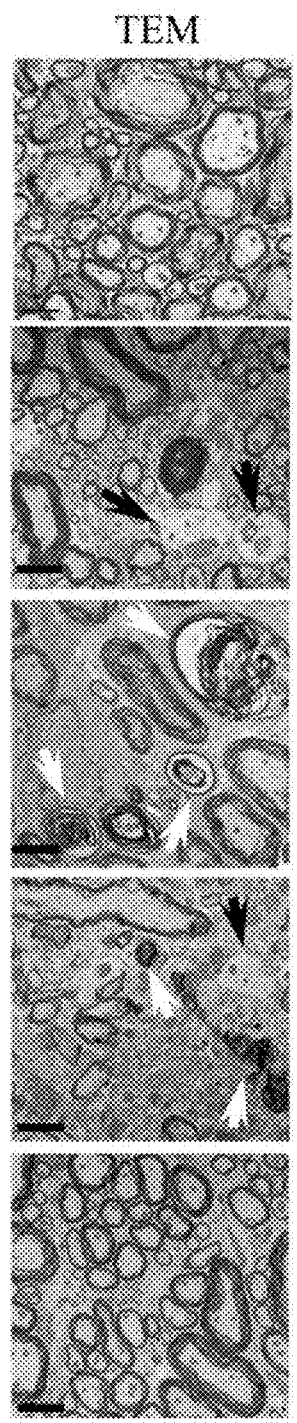

SJL/J mice were induced to develop EAE as described in materials and methods. At the remission following first disease onset, the mice were conditioned and transplanted with C57BL/6 donor bone marrow cells to induce mixed chimerism. The EAE mice without treatment (model control) or treated with conditioning alone had relapses about 2 weeks later, and there was no significant difference in clinical disease scores between the two groups (FIG. 3A). In contrast, the mixed chimeric EAE mice showed no relapse and appeared to be healthy (P<0.01, FIG. 3A). Further, by fast blue staining the myelin sheath in EAE mice before conditioning was compared with that with or without induction of mixed chimerism at 75 days after HCT. Compared with normal spinal cord tissue, there was about 10% area of demyelination in the mice before conditioning, and as time went on, the model control mice and the conditioning-alone mice had about 15% area of demyelination; in contrast, the mixed chimeras showed no demyelination at all (P<0.01, FIGS. 3B and 3C). In addition, analysis with EM showed that there were demyelinated axons before conditioning, and there were not only demyelinated axons but also destroyed axons in the model control mice and conditioning-alone mice. In contrast, there were no damaged axons or demyelination in the tissues of mixed chimeras (FIG. 3D). These results indicate that induction of mixed chimerism was able to prevent axon damage and augment myelin regeneration.

Example 3: Induction of Mixed Chimerism in EAE Mice

This example demonstrates that induction of mixed chimerism reversed autoimmunity and eliminated lymphocyte infiltration in spinal tissue.

Figure 4A:
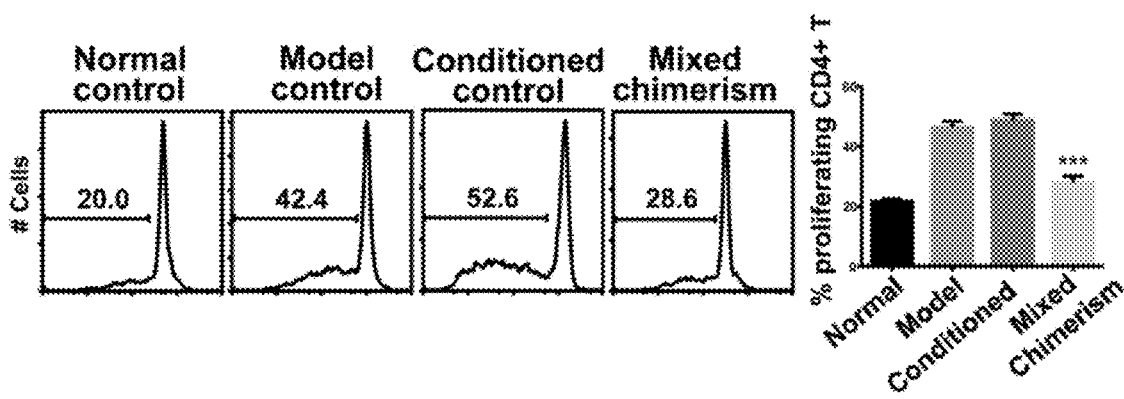
FIGS. 4A-4D show induction of mixed chimerism reversed autoimmunity and eliminated tissue infiltration. At day 75 after HCT, sorted splenic host-type $CD4^+$ T cells from mixed chimeras and control mice were labeled with CFSE and stimulated with syngeneic DCs pulsed with myelin peptide in vitro for 3 days.
Figure 4B:
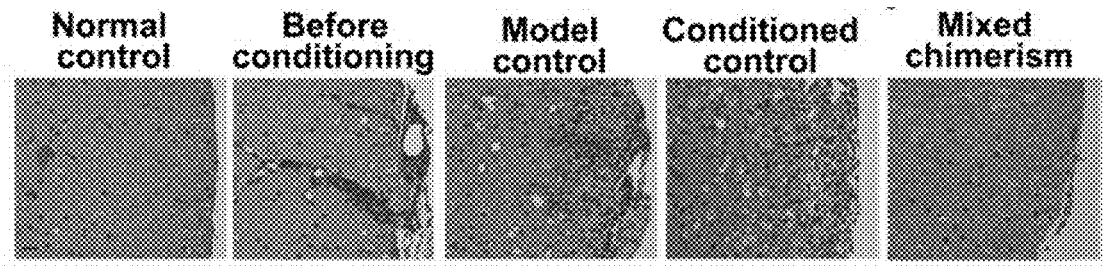
Figure 4C:
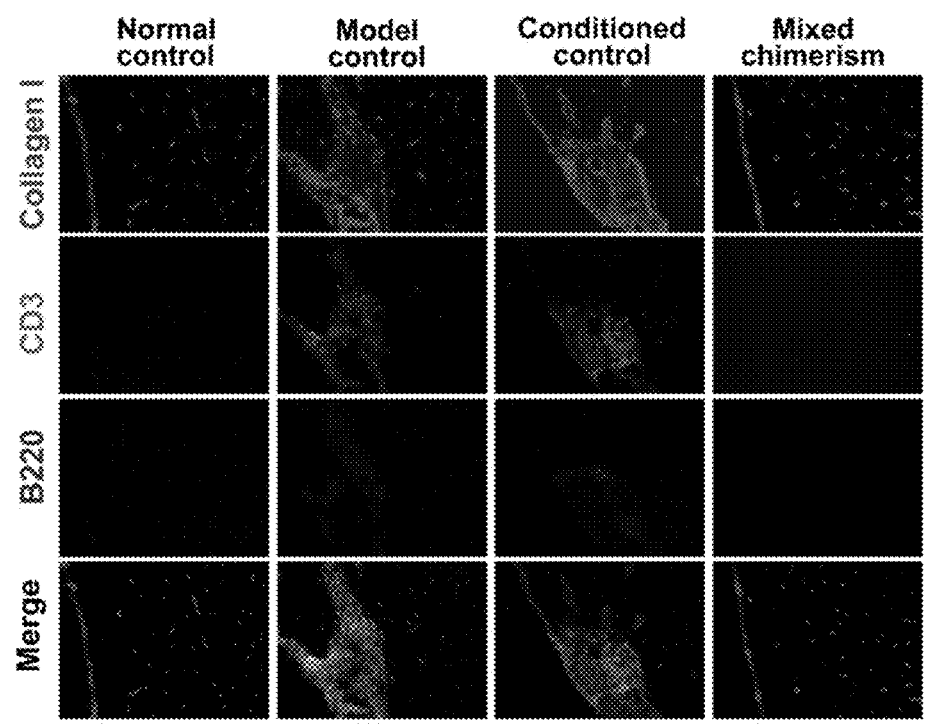
Figure 4D:
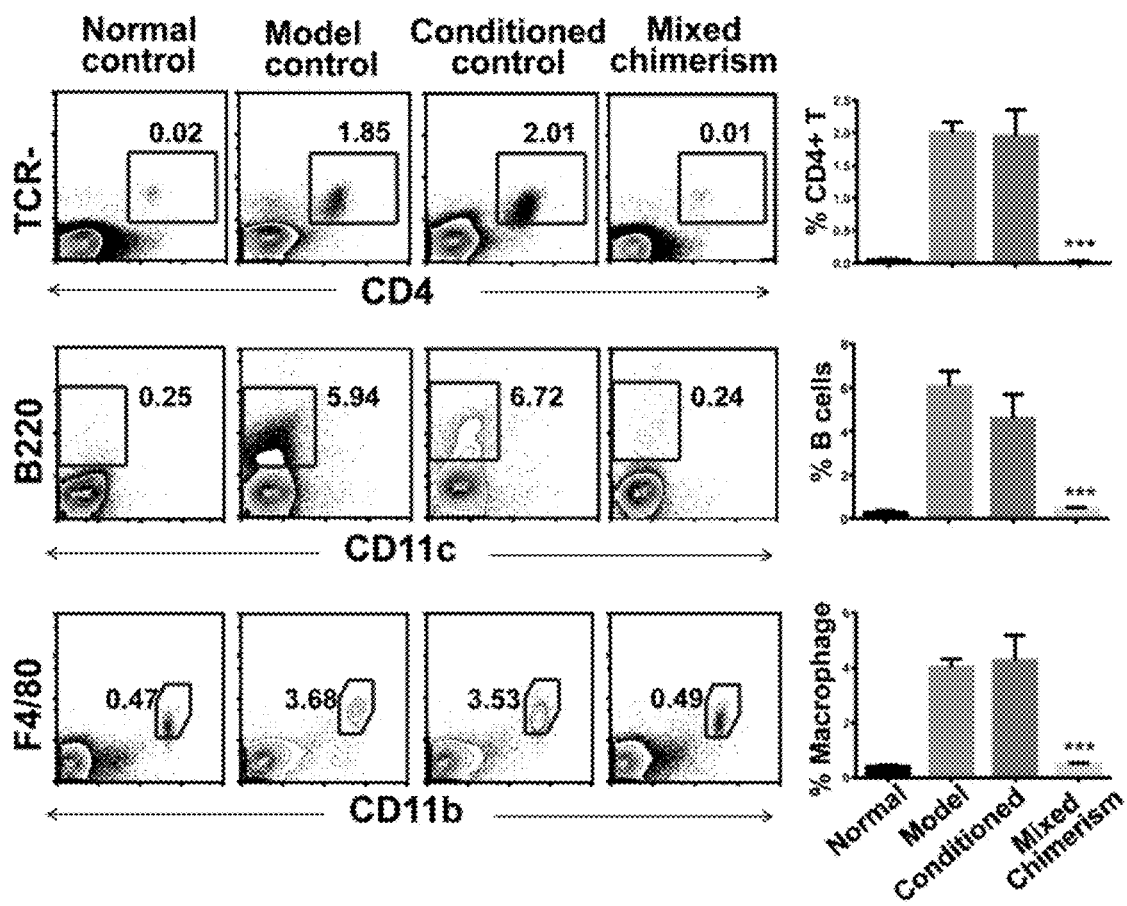

Since EAE is mediated by myelin peptide reactive T cells (5), the autoreactivity of host-type CD4+ T cells was measured in the mixed chimeras, and CD4+ T cells from normal mice, and untreated EAE mice or conditioning-treated EAE mice were used as control. It was found that CD4+ T cells from control EAE mice proliferated actively in response to stimulation by myelin peptide-loaded DCs. In contrast, host-type CD4+ T cells from the mixed chimeras had significantly reduced proliferation as compared to control CD4+ T cells ($P<0.01$), which was similar to CD4+ T cells from normal mice ($P>0.1$, FIG. 4A). Consistently, while there was severe infiltration in the spinal tissues of untreated or conditioning-treated EAE mice, there was no infiltration in the tissue of mixed chimeras, which appeared identical to normal tissue (FIG. 4B). It was reported that ectopic lymphoid tissues consisting of Collagen I, T and B cells occurs in chronic EAE mice (51). In this disclosure, ectopic lymphoid tissues in the spinal tissues of untreated or conditioning-treated EAE mice was observed, but not in the tissues of mixed chimeric mice (FIG. 4C). Finally, infiltrating CD4+ T, B and macrophages in the spinal cord tissues of EAE mice were eliminated in the mixed chimeras as determined by flow cytometry analysis of infiltrating cells ($P<0.001$, FIG. 4D). These results demonstrate that induction of mixed chimerism with MHC-mismatched donor bone marrow cells was able to eliminate tissue inflammation of EAE.

Example 4: Induction of Mixed Chimerism in EAE Mice

This example demonstrates that induction of mixed chimerism reduced Th17 and increased host-type Treg as well as increased thymic Treg production.

Figure 5A:
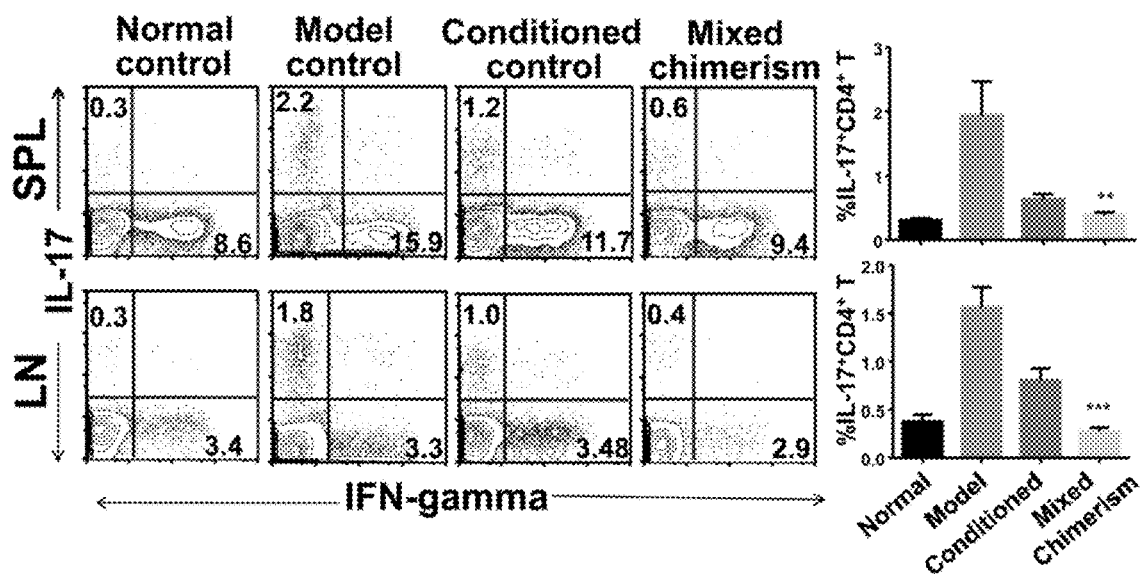
FIGS. 5A-5C show that induction of mixed chimerism reduced Th17 and increased Treg of host-type as well as increased thymic Treg production. At day 75 after HCT, percentage of $IL-17^+$, $IFN-\gamma^+$ and $Foxp3^+$ T cells in spleen, lymph nodes (LN) and thymus were measured by flow cytometry; one representative flow cytometry pattern is shown of 6 replicate experiments. Mean±SE of 6 replicate experiments is shown.
Figure 5B:
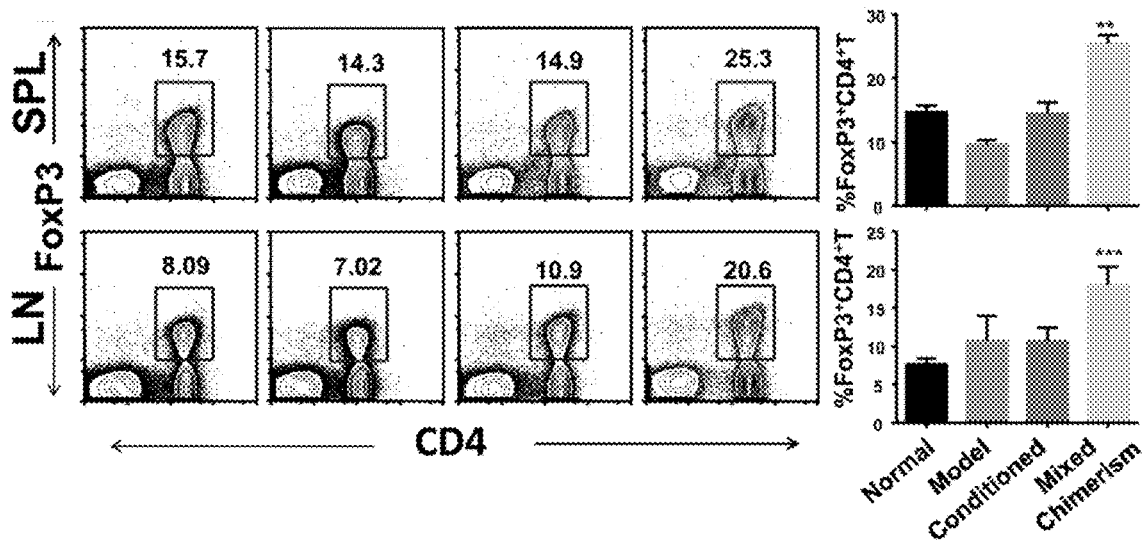

Autoreactive Th17 cells play a critical role in mediating EAE and Foxp3+ Treg cells play an important role in preventing EAE (52). Thus the impact of induction of mixed chimerism on the changes in percentages of Th17 and Treg among host-type CD4+ T cells in the spleen and spinal cord draining lymph nodes was evaluated. As compared to untreated EAE mice, conditioning alone significantly reduced the percentage of Th17 among host-type CD4+ T cells in the spleen and lymph nodes ($P<0.01$), but the percentage of Th17 was still significantly higher than normal mice ($P<0.01$, FIG. 5A), and conditioning alone did not prevent EAE relapse (FIG. 3A). Compared to EAE mice treated with conditioning alone, induction of mixed chimerism significantly reduced the percentage of host-type Th17 in the spleen and lymph nodes, especially in the lymph nodes ($P<0.01$, FIG. 5A). Interestingly, as compared to untreated EAE mice, conditioning alone or induction of mixed chimerism did not significantly change the percentage of Th1 cells in the lymph nodes, although it slightly reduced the percentage of IFN-γ+CD4+ T cells in the spleen (FIG. 5A). As compared to untreated EAE mice, conditioning alone did not significantly increase the percentage of Foxp3+ Treg cells in the spleen or lymph nodes. In contrast, induction of mixed chimerism significantly increased the percentage of Treg cells among host-type CD4+ T cells in both the spleen and lymph nodes ($P<0.01$, FIG. 5B). Therefore, induction of mixed chimerism resulted in reduction of Th17 but an increase of Treg cells among host-type CD4+ T cells in the peripheral lymphoid tissues, especially in the draining lymph nodes.

Figure 5C:
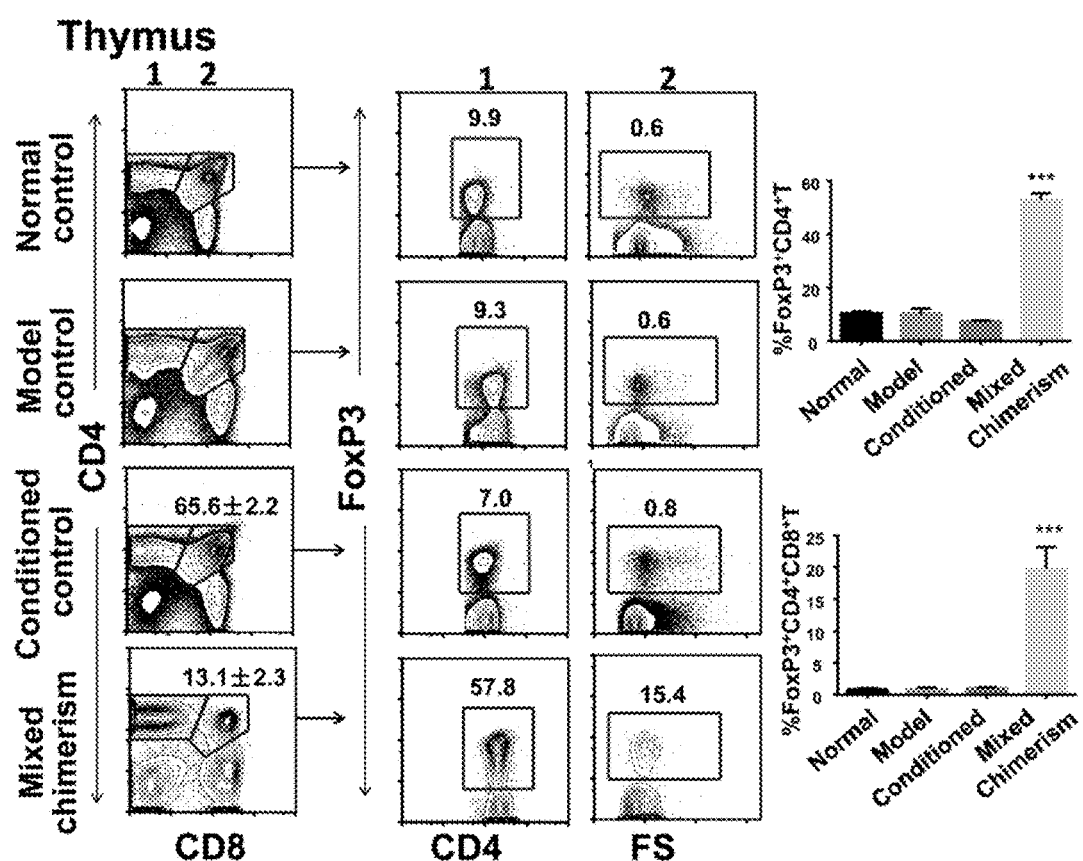

Thymic derived natural Treg cells play a critical role in regulating systemic autoimmunity (53), although adaptive Treg cells derived from conventional CD4+ T cells also play a role (54). Thymic Treg cells begin expressing Foxp3 at the late-stage of CD4+CD8+ thymocyte development (55). The percentage of Foxp3+ Treg cells among CD4+ thymocyte and CD4+CD8+ thymocytes was compared. It was found that, as compared to untreated EAE mice, conditioning treatment alone did not have a significant impact on the percentage of Treg cells in the thymus (FIG. 5C). Surprisingly, induction of mixed chimerism increased Treg cells by about 8-fold among CD4+ thymocytes and by about 20-fold among CD4+CD8+ thymocytes, as compared to EAE mice treated with conditioning alone ($P<0.01$, FIG. 5C). In addition, the host-type CD4+CD8+ thymocytes were markedly reduced as compared to that of recipients given conditioning alone ($P<0.01$, FIG. 5C). This reduction of CD4+CD8+ thymocytes in mixed chimeric autoimmune EAE was consistent with a similar reduction previously seen in mixed chimeric autoimmune NOD mice, although there was no significant increase of percentage of Foxp3+ cells among CD4+CD8+ thymocytes in the latter chimeras (34).

Figure 6:
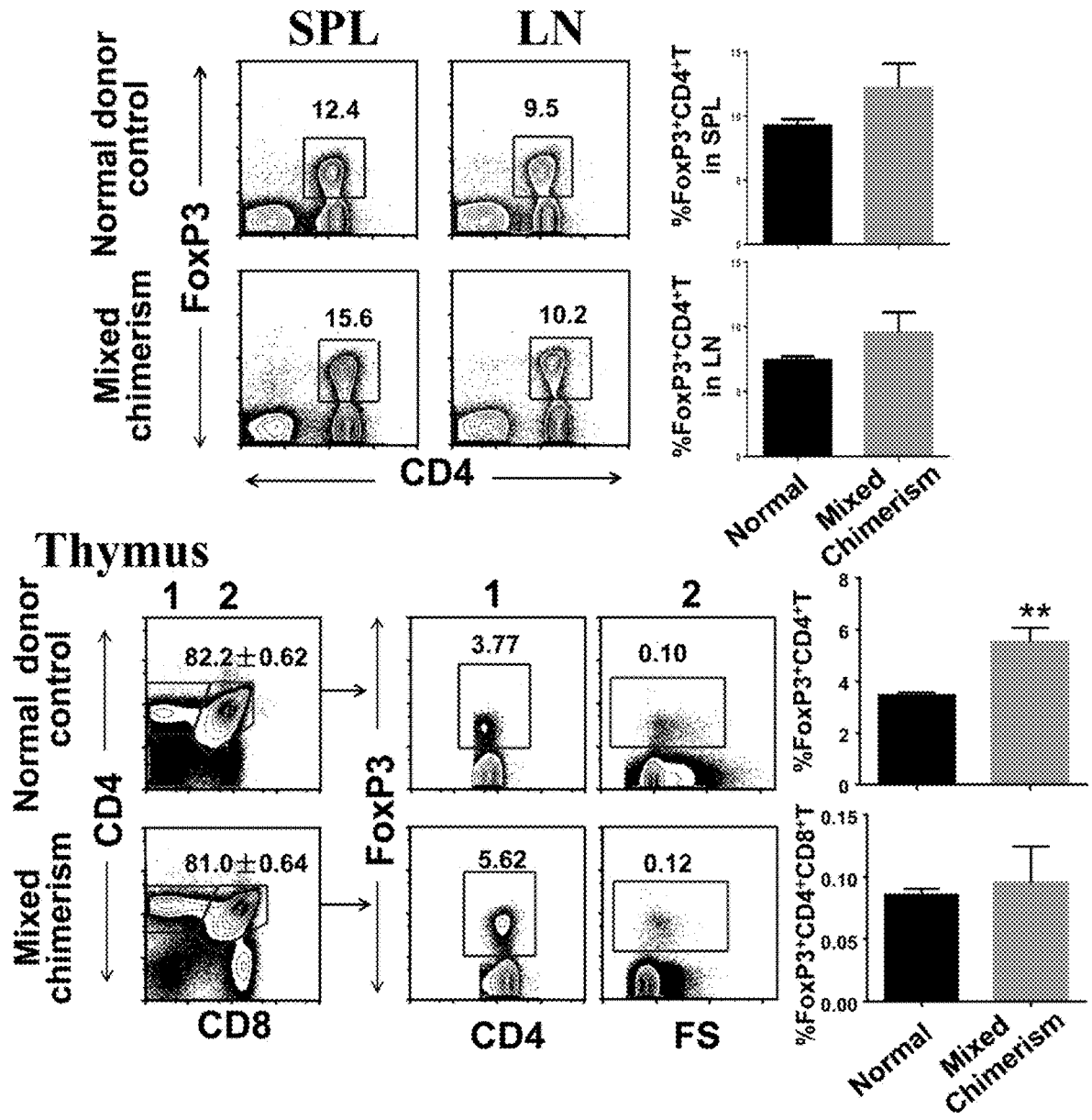
FIG. 6 shows that induction of mixed chimerism did not increase the percentage of donor-type Treg cells as compared to normal donors. At day 75 after HCT, the percentage of $CD4^+$ $FoxP3^+$ Treg cells among T cells in the spleen and lymph nodes and the percentage of $Foxp3^+$cells among $CD4^+CD8^-$ and $CD4^+CD8^+$ thymocytes were measured by flow cytometry. One representative flow cytometry pattern is shown of 6 replicate experiments. Mean±SE of 6 replicate experiments is shown.
Figure 7:
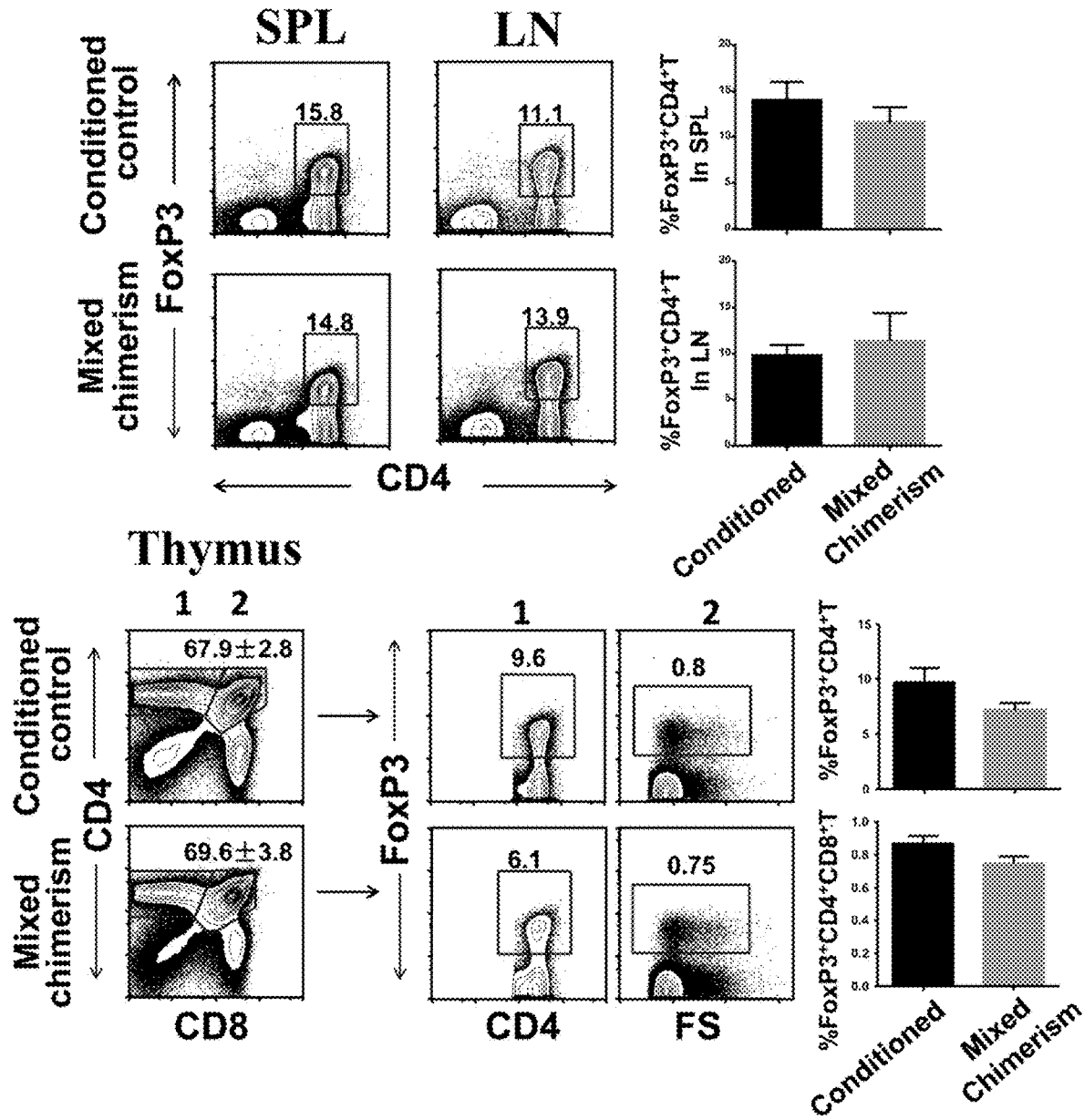
FIG. 7 shows that induction of mixed chimerism in normal SJL/J mice without EAE disease did not increase the percentage of host-type Treg cells. At day 75 after HCT, the percentage of host-type $CD4^+FoxP3^+$ Treg cells among host-type T cells in the spleen and spinal draining LN as well as percentage of $FoxP3^+$ Treg cells among $CD4^+CD8^-$ and $CD4^+CD8^+$ thymocytes were measured by flow cytometry; one representative flow cytometry pattern is shown of 6 replicate experiments. Mean±SE of 6 replicate experiments is shown.

The percentage of Foxp3+ cells among donor-type CD4+ T cells in the mixed chimeric EAE mice was measured, using the normal donor mice as control. Induction of mixed chimerism did not increase the percentage of donor-type CD4+Foxp3+ Treg cells among donor-type T cells in the spleen, spinal draining LN, or CD4+CD8+ thymocytes of the mixed chimeras ($P>0.1$), although there was an significant increase among CD4+CD8− donor-type thymocytes ($P<0.05$, FIG. 6). There was no difference in the percentage of donor-type CD4+CD8+ thymocytes, either (FIG. 6). In addition, it was observed that induction of mixed chimerism with the same conditioning and with C57BL/6 donor transplants in the normal SJL/J mice without induction of EAE did not increase the percentage of CD4+Foxp3+ Treg cells among host-type T cells in the spleen or spinal draining LN, or among host-type CD4+CD8+ thymocytes (FIG. 7). Similarly, induction of mixed chimerism did not reduce the percentage of host-type CD4+CD8+ thymocytes (FIG. 7). Taken together, these results indicate that induction of mixed chimerism augmented negative selection of CD4+CD8+ thymocytes and augmented thymic generation of Treg cells in EAE SJL/J mice.

Example 5: Induction of Mixed Chimerism in EAE Mice

This example demonstrates that induction of mixed chimerism in thymectomized recipients did not prevent EAE relapse but reduced severity of relapse.

Figure 8A:
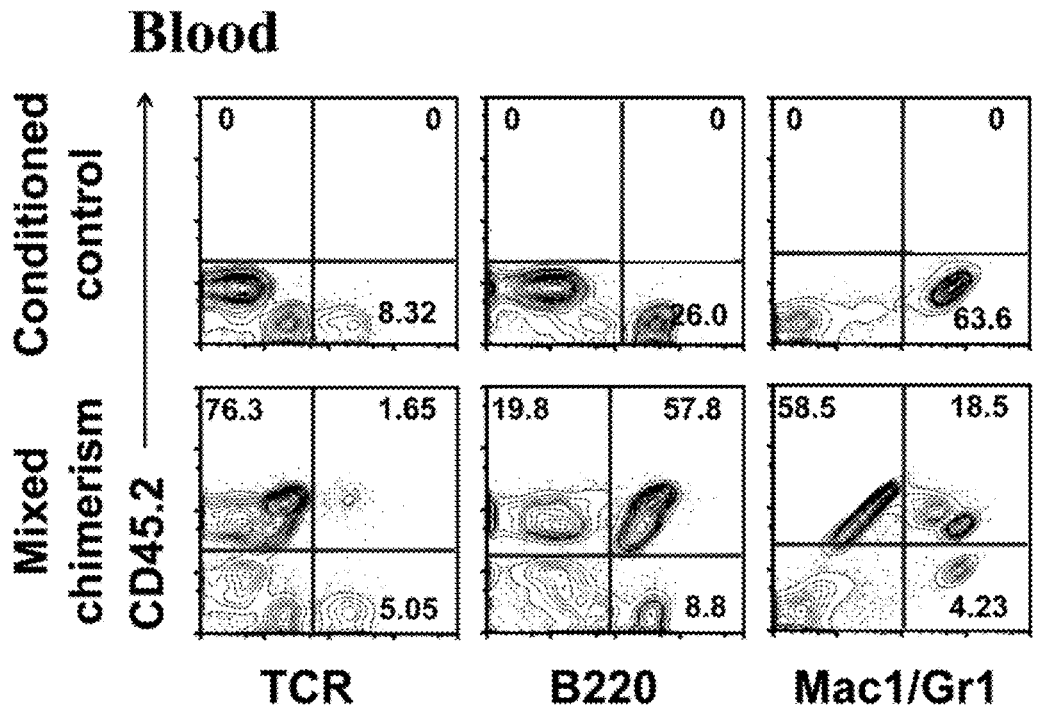
FIGS. 8A-8C show representative patterns of mixed chimerism in thymectomized mice. At day 75 after HCT, mononuclear cells from blood (FIG. 8A), spleen (FIG. 8B), and bone marrow (FIG. 8C) of mixed chimeras and control thymectomized mice given conditioning only were analyzed for the percentage of donor-type ($CD45.2^+$) and host-type ($CD45.1^+$) cells among T cells ($TCR\beta^+$), B cells ($B220^+$), and myeloid cells ($Mac-1^+/Gr-1^+$). One representative is shown of 4 replicate experiments.
Figure 8B:
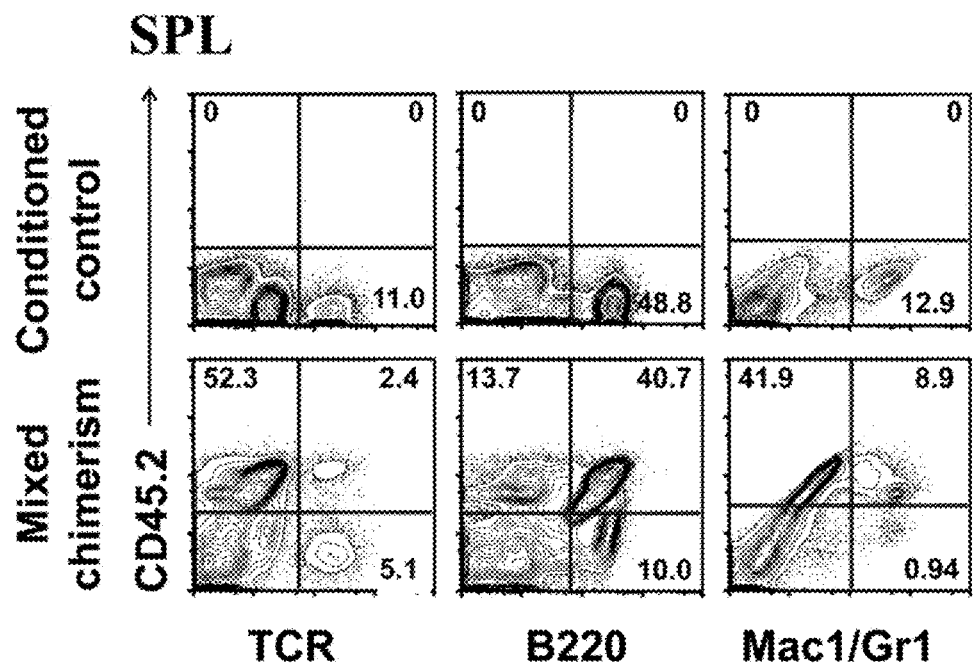
Figure 8C:
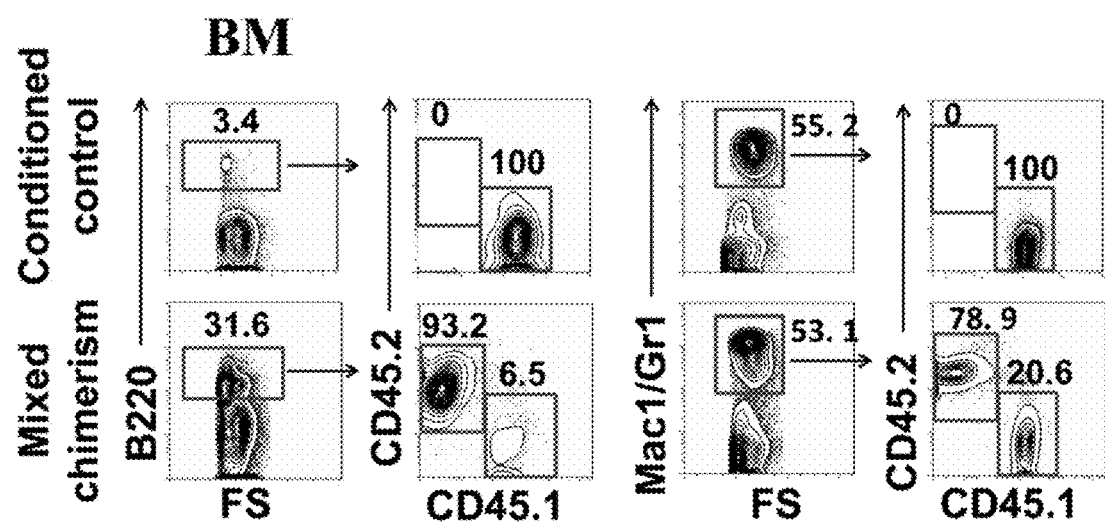

The thymus' role in prevention of EAE was evaluated using thymectomized EAE mice. Accordingly, adult thymectomized SJL/J mice were induced to develop EAE and then induced to develop mixed chimerism (FIGS. 8A-8C). It was found that induction of mixed chimerism was not able to prevent relapse of EAE, although it was able to significantly reduce the disease severity ($P<0.01$, FIG. 9A). As compared to EAE mice given conditioning alone, induction of mixed chimerism only partially reduced demyelination ($P<0.05$, FIGS. 9B and 9C). Although induction of mixed chimerism appeared to reduce tissue infiltration, there was still obvious infiltration under the spinal cord membrane (FIG. 9D).

Figure 10A:
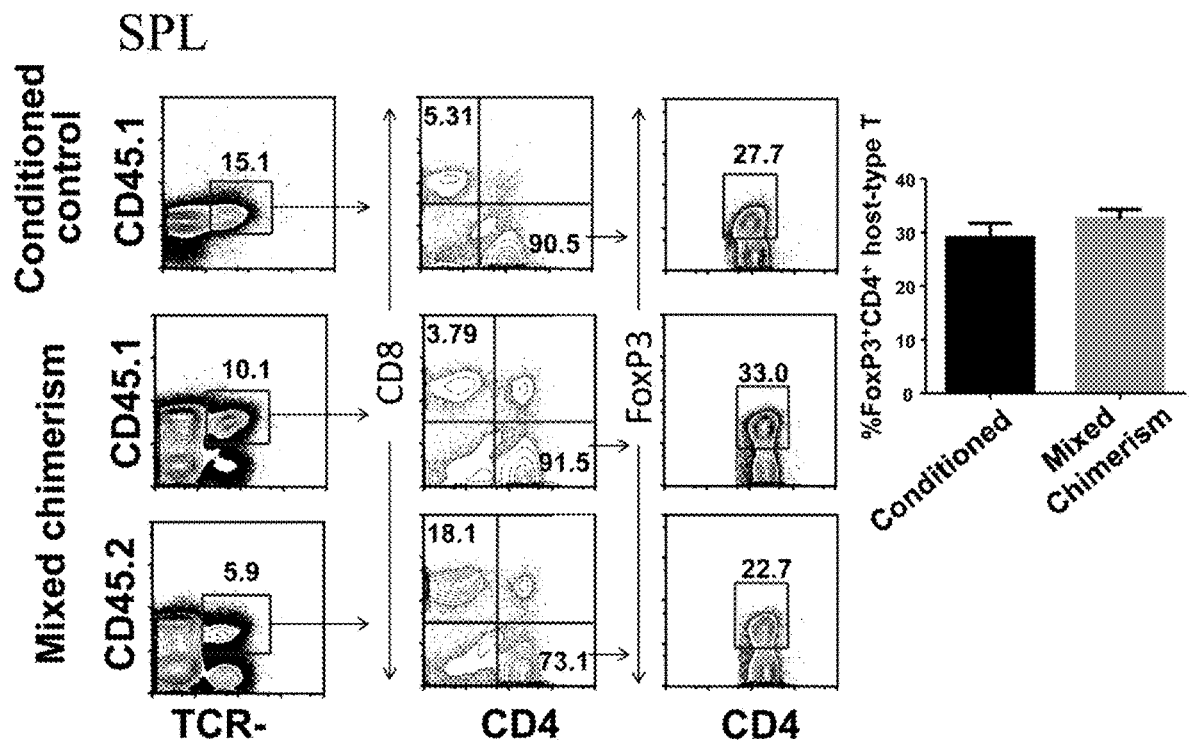
FIGS. 10A-10B show that induction of mixed chimerism in thymectomized EAE mice augmented Foxp3$^+$ Treg expansion. At day 75 after HCT, the percentage of host and donor-type Foxp3$^+$ CD4$^+$ T cells in spleen and LN of thymectomized EAE mice were measured by flow cytometry.
Figure 10B:
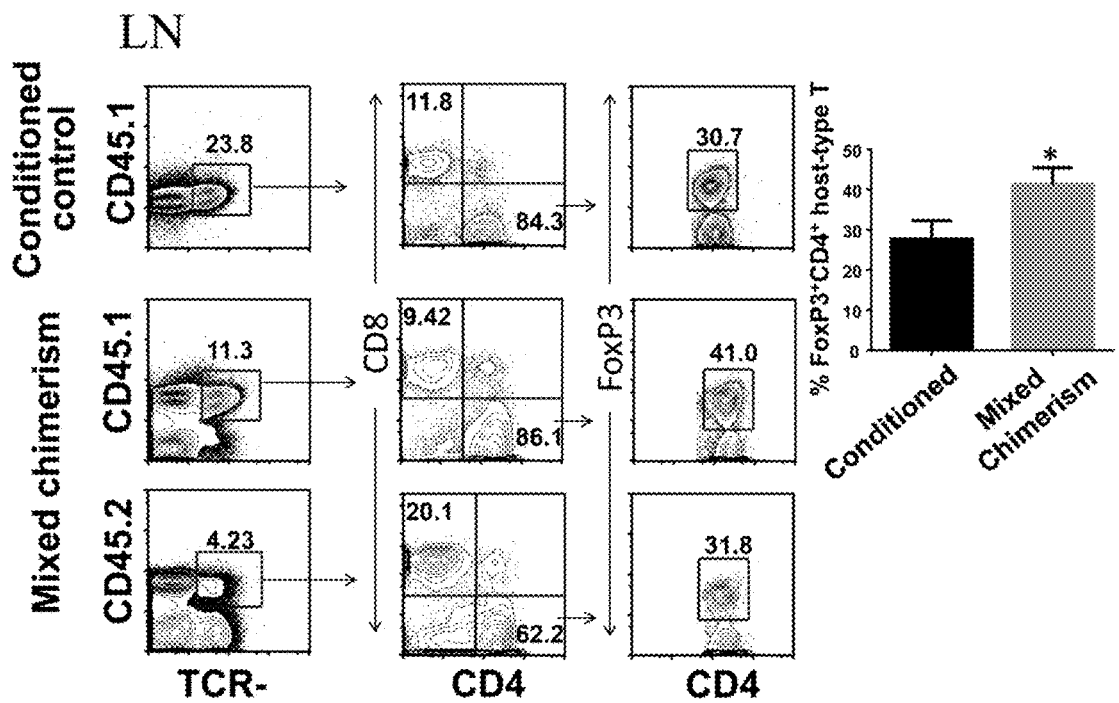

The percentage of Foxp3+ cells among host-type CD4+ T cells in the EAE mice treated with conditioning alone or with induction of mixed chimerism was measured. In the spleen of mixed chimeras, the percentage of Foxp3+ Treg cells among CD45.1+ host-type CD4+ T cells was about 30%, and there was no significant difference between EAE mice treated with conditioning alone or induction of mixed chimerism. The percentage of Foxp3+ Treg cells among CD45.2+ donor-type CD4+ T cells was about 25% (FIG. 10A). On the other hand, the percentage of Foxp3+ Treg cells among CD45.1+ host-type CD4+ T cells in the spinal draining LN of mixed chimeras reached about 40%, which was significantly higher than in recipients given conditioning alone (P<0.05, FIG. 10B). The percentage of Foxp3+ cells among CD45.2+ donor-type CD4+ T cells was about 30% (FIG. 10B). These results indicate that induction of mixed chimerism in thymectomized EAE mice was able to augment expansion of Foxp3+ Treg cells in the periphery, especially in the spinal draining LN, but the expansion of Treg cells was not sufficient to prevent autoimmune EAE.

Example 6: Induction of Mixed Chimerism in EAE Mice

This example demonstrates that induction of mixed chimerism in late-stage EAE mice eliminated infiltration in spinal tissues but did not cure diseases.

Figure 11A:
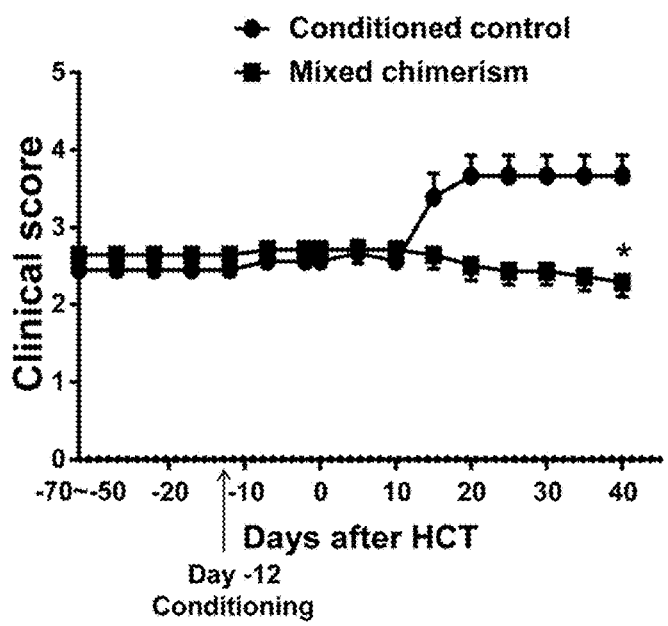
FIGS. 11A-11D show that induction of mixed chimerism in late-stage EAE mice eliminated infiltration in spinal tissues and partially improved demyelination but did not cure disease. EAE mice with multiple relapses and persistent high clinical score (>2.5) for more than 20 days were conditioned and induced to develop mixed chimerism as described in FIGS. 3A-3D.
Figure 11B:
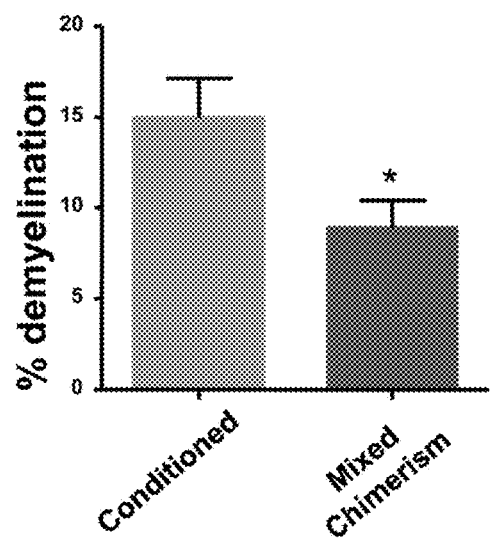
Figure 11C:
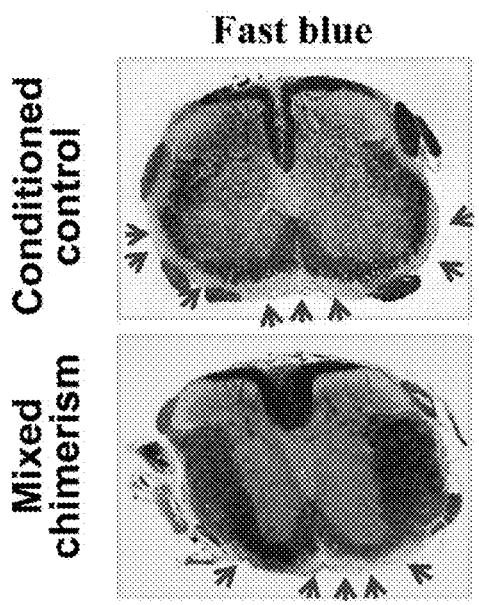
Figure 11D:
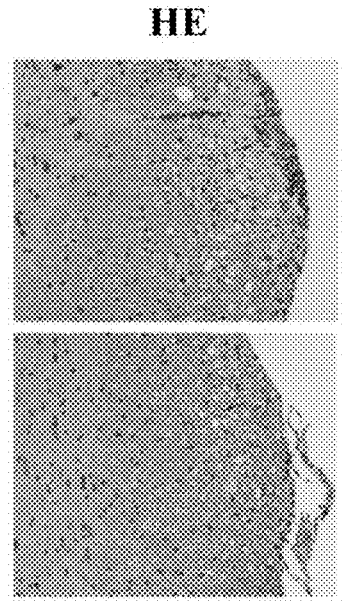

Finally, induction of mixed chimerism was evaluated to see whether it was able to reverse late-stage EAE. EAE mice with multiple relapses and persistent high clinical score (≥2.5) for more than 20 days were defined as late-stage. The experiments were ended at 50 days after HCT following the mandate of the IACUC. It was found that, compared to conditioning alone, induction of mixed chimerism only prevented the worsening of the disease (P<0.01,) but did not reverse the disease (FIG. 11A). Although induction of mixed chimerism was able to clear tissue infiltration and significantly reduce demyelination, it was not able to adequately promote remyelination (FIGS. 11B-D). This may be due to the damage of axon at this late-stage, as suggested by holes in the white matter area (FIG. 11D).

Example 7: Induction of Mixed Chimerism in Late-Stage Diabetic NOD Mice

This example demonstrates that radiation-free conditioning regimen with CY, PT and ATG induced mixed chimerism in late-stage diabetic NOD mice.

Late-stage diabetic NOD mice were conditioned and induced for mixed chimerism with a regimen consisting of clinically available reagents including CY, PT and ATG, as described in FIG. 12A. In brief, late-stage diabetic NOD mice were conditioned with i.p. injection of CY (50 mg/Kg) daily for 12 days, PT (1 mg/Kg) every 4 days for a total 4 injections, and ATG (25 mg/Kg) every 4 days for 3 injections. On day 0, recipients were transplanted with bone marrow (BM) cells (50×10$^6$) and CD4+ T-depleted spleen cells (25×10$^6$) from MHC-mismatched C57BL/6 (H-2$^b$) donors. After HCT, the recipients were checked for chimerism monthly by staining peripheral blood mononuclear cells with fluorescently labeled anti-donor marker antibody (anti-H-2$^b$). It was found that 30% (21/69) of recipients conditioned with CY, PT, and ATG developed complete chimerism, 54% (37/69) developed mixed chimerism, and 16% (11/69) did not develop chimerism (FIG. 12B) 60 days after HCT. These results indicate that conditioning with CY, PT, and ATG together induced stable mixed chimerism when transplanting bone marrow and CD4+ T-depleted spleen cells from MHC-mismatched donors in late-stage diabetic NOD mice.

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Steinman L (2014) Immunology of relapse and remission in multiple sclerosis. *Annu Rev Immunol* 32:257-281.
2. Sospedra M & Martin R (2005) Immunology of multiple sclerosis. *Annu Rev Immunol* 23:683-747.
3. Trapp B D & Nave K A (2008) Multiple sclerosis: an immune or neurodegenerative disorder? *Annual review of neuroscience* 31:247-269.
4. Kuchroo V K, et al. (2002) T cell response in experimental autoimmune encephalomyelitis (EAE): role of self and cross-reactive antigens in shaping, tuning, and regulating the autopathogenic T cell repertoire. *Annu Rev Immunol* 20:101-123.
5. Kronenberg M & Rudensky A (2005) Regulation of immunity by self-reactive T cells. *Nature* 435(7042):598-604.
6. Hafler D A, et al. (2005) Multiple sclerosis. *Immunological reviews* 204:208-231.
7. Haas J, et al. (2005) Reduced suppressive effect of CD4+CD25 high regulatory T cells on the T cell immune response against myelin oligodendrocyte glycoprotein in patients with multiple sclerosis. *European journal of immunology* 35(11):3343-3352.
8. Viglietta V, Baecher-Allan C, Weiner H L, & Hafler D A (2004) Loss of functional suppression by CD4+CD25+ regulatory T cells in patients with multiple sclerosis. *The Journal of experimental medicine* 199(7):971-979.
9. Huan J, et al. (2005) Decreased FOXP3 levels in multiple sclerosis patients. *Journal of neuroscience research* 81(1): 45-52.
10. Frisullo G, et al. (2009) Regulatory T cells fail to suppress CD4T+-bet+ T cells in relapsing multiple sclerosis patients. *Immunology* 127(3):418-428.
11. Lange C, Scholl M, Melms A, & Bischof F (2011) CD62L(high) Treg cells with superior immunosuppressive properties accumulate within the CNS during remissions of EAE. *Brain, behavior, and immunity* 25(1):120-126.
12. Zozulya A L & Wiendl H (2008) The role of regulatory T cells in multiple sclerosis. *Nature clinical practice. Neurology* 4(7):384-398.
13. Atkins H L & Freedman M S (2013) Hematopoietic stem cell therapy for multiple sclerosis: top 10 lessons learned. *Neurotherapeutics: the journal of the American Society for Experimental NeuroTherapeutics* 10(1):68-76.
14. Farge D, et al. (2010) Autologous hematopoietic stem cell transplantation for autoimmune diseases: an observational study on 12 years' experience from the European Group for Blood and Marrow Transplantation Working Party on Autoimmune Diseases. *Haematologica* 95(2): 284-292.
15. Mancardi G L, et al. (2012) Autologous haematopoietic stem cell transplantation with an intermediate intensity conditioning regimen in multiple sclerosis: the Italian multi-centre experience. *Multiple sclerosis* 18(6):835-842.
16. Bowen J D, et al. (2012) Autologous hematopoietic cell transplantation following high-dose immunosuppressive therapy for advanced multiple sclerosis: long-term results. *Bone marrow transplantation* 47(7):946-951.
17. Krasulova E, et al. (2010) High-dose immunoablation with autologous haematopoietic stem cell transplantation in aggressive multiple sclerosis: a single centre 10-year experience. *Multiple sclerosis* 16(6):685-693.
18. Fassas A, et al. (2011) Long-term results of stem cell transplantation for MS: a single-center experience. *Neurology* 76(12):1066-1070.
19. Daikeler T, et al. (2011) Secondary autoimmune diseases occurring after HSCT for an autoimmune disease: a retrospective study of the EBMT Autoimmune Disease Working Party. *Blood* 118(6):1693-1698.
20. Pasquini M C, et al. (2010) Hematopoietic stem cell transplantation for multiple sclerosis: collaboration of the CIBMTR and EBMT to facilitate international clinical studies. *Biology of blood and marrow transplantation: journal of the American Society for Blood and Marrow Transplantation* 16(8):1076-1083.
21. Griffith L M, et al. (2005) Feasibility of allogeneic hematopoietic stem cell transplantation for autoimmune disease: position statement from a National Institute of Allergy and Infectious Diseases and National Cancer Institute-Sponsored International Workshop, Bethesda, MD, Mar. 12 and 13, 2005. *Biology of blood and marrow transplantation: journal of the American Society for Blood and Marrow Transplantation* 11(11):862-870.
22. Lu J Q, et al. (2009) Continued disease activity in a patient with multiple sclerosis after allogeneic hematopoietic cell transplantation. *Archives of neurology* 66(1):116-120.
23. Scandling J D, et al. (2012) Tolerance and withdrawal of immunosuppressive drugs in patients given kidney and hematopoietic cell transplants. *American journal of transplantation: official journal of the American Society of Transplantation and the American Society of Transplant Surgeons* 12(5):1133-1145.
24. Sykes M & Nikolic B (2005) Treatment of severe autoimmune disease by stem-cell transplantation. *Nature* 435(7042):620-627.
25. Nikolic B, et al. (2004) Mixed hematopoietic chimerism allows cure of autoimmune diabetes through allogeneic tolerance and reversal of autoimmunity. *Diabetes* 53(2): 376-383.
26. Beilhack G F, Landa R R, Masek M A, & Shizuru J A (2005) Prevention of type 1 diabetes with major histocompatibility complex-compatible and nonmarrow ablative hematopoietic stem cell transplants. *Diabetes* 54(6): 1770-1779.
27. Shizuru J (2004) The Experimental Basis for Hematopoietic Cell Transplantation of Autoimmune Disease. *Thomas' Hematopoietic cell transplantation*, ed Blume K G, Forman, S. J., and Appelbaum, F. R. (Blackwell Publishing Ltd, Malden, MA), pp 324-343.
28. Ildstad S T, Chilton P M, Xu H, Domenick M A, & Ray B (2005) Preconditioning of NOD mice with anti-CD8 mAb and costimulatory blockade enhances chimerism and tolerance and prevents diabetes, while depletion of alpha beta-TCR+ and CD4+ cells negates the effect. *Blood* 105(6):2577-2584.
29. Li H, et al. (1996) Mixed allogeneic chimerism induced by a sublethal approach prevents autoimmune diabetes and reverses insulitis in nonobese diabetic (NOD) mice. *Journal of immunology* 156(1):380-388.
30. Liang Y, et al. (2005) Donor CD8+ T cells facilitate induction of chimerism and tolerance without GVHD in autoimmune NOD mice conditioned with anti-CD3 mAb. *Blood* 105(5):2180-2188.
31. Zhang C, et al. (2007) Elimination of insulitis and augmentation of islet beta cell regeneration via induction of chimerism in overtly diabetic NOD mice. *Proc Natl Acad Sci USA* 104(7):2337-2342.
32. Li N, et al. (2008) HDAC inhibitor reduces cytokine storm and facilitates induction of chimerism that reverses lupus in anti-CD3 conditioning regimen. *Proc Natl Acad Sci USA* 105(12):4796-4801.
33. Zhang C, et al. (2010) Induction of chimerism permits low-dose islet grafts in the liver or pancreas to reverse refractory autoimmune diabetes. *Diabetes* 59(9):2228-2236.
34. Racine J, et al. (2011) Induction of Mixed Chimerism With MHC-Mismatched but Not Matched Bone Marrow Transplants Results in Thymic Deletion of Host-Type Autoreactive T-Cells in NOD Mice. *Diabetes* 60(2):555-564.
35. Wang M, et al. (2012) Mixed Chimerism and Growth Factors Augment beta Cell Regeneration and Reverse Late-Stage Type 1 Diabetes. *Science translational medicine* 4(133): 133ra159.
36. Racine J J, Wang M, Zhang M, & Zeng D (2014) Induction of mixed chimerism depletes pre-existing and de novo-developed autoreactive B cells in autoimmune NOD mice. *Diabetes* 63(6):2051-2062.
37. Racine J J, et al. (2015) MHC-mismatched mixed chimerism mediates thymic deletion of cross-reactive autoreactive T cells and prevents insulitis in nonobese diabetic mice. *Journal of immunology* 194(1):407-417.
38. Wang M, et al. (2014) MHC-mismatched chimerism is required for induction of transplantation tolerance in autoimmune nonobese diabetic recipients. *Journal of immunology* 193(4):2005-2015.
39. Mariotti J, et al. (2011) The pentostatin plus cyclophosphamide nonmyeloablative regimen induces durable host T cell functional deficits and prevents murine marrow allograft rejection. *Biology of blood and marrow transplantation: journal of the American Society for Blood and Marrow Transplantation* 17(5):620-631.
40. DeZern A E, et al. (2011) High-dose cyclophosphamide without stem cell rescue in 207 patients with aplastic anemia and other autoimmune diseases. *Medicine* 90(2): 89-98.
41. Dezern A E, et al. (2013) Repeated treatment with high dose cyclophosphamide for severe autoimmune diseases. *American journal of blood research* 3(1):84-90.
42. Hassan R, et al. (2013) Major cancer regressions in mesothelioma after treatment with an anti-mesothelin immunotoxin and immune suppression. *Science translational medicine* 5(208):208ra147.
43. Luznik L, O'Donnell P V, & Fuchs E J (2012) Post-transplantation cyclophosphamide for tolerance induction in HLA-haploidentical bone marrow transplantation. *Seminars in oncology* 39(6):683-693.
44. Sauter C, Lamanna N, & Weiss M A (2008) Pentostatin in chronic lymphocytic leukemia. *Expert opinion on drug metabolism & toxicology* 4(9):1217-1222.
45. Chen S H, Ochs H D, Scott C R, Giblett E R, & Tingle A J (1978) Adenosine deaminase deficiency: disappearance of adenine deoxynucleotides from a patient's erythrocytes after successful marrow transplantation. *The Journal of clinical investigation* 62(6):1386-1389.

46. Lan F, Zeng D, Higuchi M, Higgins J P, & Strober S (2003) Host conditioning with total lymphoid irradiation and antithymocyte globulin prevents graft-versus-host disease: the role of CD1-reactive natural killer T cells. *Biology of blood and marrow transplantation: journal of the American Society for Blood and Marrow Transplantation* 9(6):355-363.
47. Scandling J D, Busque S, Shizuru J A, Engleman E G, & Strober S (2011) Induced immune tolerance for kidney transplantation. *N Engl J Med* 365(14):1359-1360.
48. Wang Z, et al. (2006) Role of IFN-gamma in induction of Foxp3 and conversion of CD4+ CD25− T cells to CD4+ Tregs. *The Journal of clinical investigation* 116(9): 2434-2441.
49. Deng R, et al. (2015) B7H1/CD80 interaction augments PD-1-dependent T cell apoptosis and ameliorates graft-versus-host disease. *Journal of immunology* 194(2):560-574.
50. Reddy J, et al. (2005) Cutting edge: CD4+CD25+ regulatory T cells contribute to gender differences in susceptibility to experimental autoimmune encephalomyelitis. *J Immunol* 175(9):5591-5595.
51. Peters A, et al. (2011) Th17 cells induce ectopic lymphoid follicles in central nervous system tissue inflammation. *Immunity* 35(6):986-996.
52. Bettelli E, Oukka M, & Kuchroo V K (2007) T(H)-17 cells in the circle of immunity and autoimmunity. *Nat Immunol* 8(4):345-350.
53. Sakaguchi S, Yamaguchi T, Nomura T, & Ono M (2008) Regulatory T cells and immune tolerance. *Cell* 133(5): 775-787.
54. Bluestone J A & Abbas A K (2003) Natural versus adaptive regulatory T cells. *Nature reviews. Immunology* 3(3):253-257.
55. Liston A, et al. (2008) Differentiation of regulatory Foxp3+ T cells in the thymic cortex. *Proceedings of the National Academy of Sciences of the United States of America* 105(33):11903-11908.
56. Krishnamoorthy G, Lassmann H, Wekerle H, & Holz A (2006) Spontaneous opticospinal encephalomyelitis in a double-transgenic mouse model of autoimmune T cell/B cell cooperation. *The Journal of clinical investigation* 116(9):2385-2392.
57. Schmidt D, Verdaguer J, Averill N, & Santamaria P (1997) A mechanism for the major histocompatibility complex-linked resistance to autoimmunity. *The Journal of experimental medicine* 186(7):1059-1075.
58. Wu T, et al. (2013) Thymic damage, impaired negative selection, and development of chronic graft-versus-host disease caused by donor CD4+ and CD8+ T cells. *Journal of immunology* 191(1):488-499.
59. Jordan M S, et al. (2001) Thymic selection of CD4+ CD25+ regulatory T cells induced by an agonist self-peptide. *Nature immunology* 2(4):301-306.
60. Gagnerault M C, et al. (2009) Autoimmunity during thymectomy-induced lymphopenia: role of thymus ablation and initial effector T cell activation timing in nonobese diabetic mice. *Journal of immunology* 183(8):4913-4920.
61. Mitchell A J, Benito-Leon J, Gonzalez J M, & Rivera-Navarro J (2005) Quality of life and its assessment in multiple sclerosis: integrating physical and psychological components of wellbeing. *The Lancet. Neurology* 4(9): 556-566.

What is claimed is:

1. A method of conditioning a recipient for transplantation comprising administering to the recipient low-doses of cyclophosphamide (CY), pentostatin (PT), and anti-thymocyte globulin (ATG), wherein the dose for CY is from about 150 mg to about 750 mg per day in human, the dose for PT is from about 2 mg/m$^2$/dose to about 8 mg/m$^2$/dose in human, and the dose for ATG is from 1.0 mg/kg/day to about 8.0 mg/kg/day in human.

2. The method of claim 1, wherein the low-doses of CY, PT, and ATG are administered to the recipient before transplantation.

3. The method of claim 1, wherein the transplantation is bone marrow transplantation, tissue transplantation, or organ transplantation.

4. A method of promoting transplantation immune tolerance in a recipient of transplantation comprising administering to the recipient low-doses of cyclophosphamide (CY), pentostatin (PT), and anti-thymocyte globulin (ATG), wherein the dose for CY is from about 150 mg to about 750 mg per day in human, the dose for PT is from about 2 mg/m$^2$/dose to about 8 mg/m$^2$/dose in human, and the dose for ATG is from 1.0 mg/kg/day to about 8.0 mg/kg/day in human.

5. The method of claim 4, wherein the low-doses of CY, PT, and ATG are administered to the recipient before transplantation.

6. The method of claim 4, wherein the transplantation is bone marrow transplantation, tissue transplantation, or organ transplantation.

7. The method of claim 1, wherein CY, PT and ATG are administered simultaneously.

8. The method of claim 3, wherein the donor bone marrow cells are CD4+ T cell depleted bone marrow cells.

9. The method of claim 4, wherein CY, PT and ATG are administered simultaneously.

10. The method of claim 6, wherein the donor bone marrow cells are CD4+ T cell depleted bone marrow cells.

* * * * *